US011998627B2

(12) United States Patent
Jarman et al.

(10) Patent No.: US 11,998,627 B2
(45) Date of Patent: Jun. 4, 2024

(54) COMPOSITIONS, PRODUCTS, SYSTEM, AND METHOD FOR PERMING HAIR

(71) Applicant: Curl Cult LLC and LISAP Laboratori Cosmetici Spa, Los Angeles, CA (US)

(72) Inventors: Janine Jarman, Glendale, CA (US); Lucca Papetti, Milan (IT)

(73) Assignee: Curl Cult LLC, Los Angeles, CA (US)

( * ) Notice: Subject to any disclaimer, the term of this patent is extended or adjusted under 35 U.S.C. 154(b) by 0 days.

(21) Appl. No.: 17/888,242

(22) Filed: Aug. 15, 2022

(65) Prior Publication Data

US 2024/0050345 A1 Feb. 15, 2024

(51) Int. Cl.
| *A61K 8/46* | (2006.01) |
| *A45D 7/04* | (2006.01) |
| *A61K 8/22* | (2006.01) |
| *A61K 8/39* | (2006.01) |
| *A61K 8/44* | (2006.01) |
| *A61K 8/64* | (2006.01) |
| *A61Q 5/04* | (2006.01) |

(52) U.S. Cl.
CPC .............. *A61K 8/46* (2013.01); *A45D 7/04* (2013.01); *A61K 8/22* (2013.01); *A61K 8/39* (2013.01); *A61K 8/44* (2013.01); *A61K 8/645* (2013.01); *A61Q 5/04* (2013.01); *A61K 2800/30* (2013.01); *A61K 2800/33* (2013.01)

(58) Field of Classification Search
CPC ... A61K 7/09; A61K 7/11; A61K 8/46; A61K 8/64; A61K 8/42; A61Q 5/04
USPC ........................................................ 424/71
IPC ...................................................... A61Q 5/00
See application file for complete search history.

(56) References Cited

U.S. PATENT DOCUMENTS

| 3,864,476 | A | * | 2/1975 | Altieri | A61K 8/23 424/70.4 |
| 4,172,887 | A | * | 10/1979 | Vanlerberghe | A61Q 5/12 424/DIG. 2 |
| 4,377,174 | A | * | 3/1983 | Muraji | A45D 7/06 132/207 |
| 5,046,515 | A | * | 9/1991 | Heinz | A61Q 5/04 132/207 |
| 5,208,014 | A | * | 5/1993 | Dubief | A61K 8/39 424/78.37 |
| 6,378,530 | B1 | * | 4/2002 | Rezvani | A61Q 5/04 424/70.2 |
| 9,713,583 | B1 | * | 7/2017 | Pressly | A61K 8/19 |

OTHER PUBLICATIONS

Create Professional, "Cuenic 1/2." https://www.shopcreatepro.com>cuenic-cuenic-1-2. Published online Mar. 29, 2018. (Year: 2018 ).*

Avalon Institute, "The types of Perms." https://avalon.edu>2014>April. Published online Apr. 4, 2014 (Year: 2014).*

* cited by examiner

*Primary Examiner* — Walter E Webb
(74) *Attorney, Agent, or Firm* — Eric Kelly

(57) ABSTRACT

Compositions, products, systems, kits, and methods of perming hair may include a first-product (perming lotion) that contains cysteamine and cysteine, such that the first-product is used to break preexisting disulfide bonds in hair, and then a second-product may be applied directly over (on top of) the first-product to neutralize the effects of the first-product without first rinsing the hair to remove the first-product, so that disulfide bonds in the hair may form to set the treated hair into a desired shape with desired curls, waves, texture, and/or style. Various on-the-rod, off-the-rod, and/or perm tools may be used to maintain the hair in the desired shape until the first-product and the second-product have finished acting on the hair and/or on each other. The Compositions, products, systems, kits, and methods of perming hair are vegan, cruelty free, paraben free, sulfate surfactant free, use minimal water, and are without thioglycolic acid.

16 Claims, 20 Drawing Sheets

Table 1: At least some details of First-Product 101

| | Ingredient | Function, role, and/or purpose | Concentration (% by mass) |
|---|---|---|---|
| 1 | Water | Solvent and/or carrier | 75-100 |
| 2 | Cysteamine HCl | Hair waving agent | 5-10 |
| 3 | PEG-40 hydrogenated castor oil | Surface active agent | 1-5 |
| 4 | Polysorbate 20 | Surface active agent | 1-5 |
| 5 | Fragrance (perfume) | Fragrance (desired odor/smell) | 1-5 |
| 6 | Imidazolidinyl urea | Preservative agent | 0.1-1 |
| 7 | Tetrasodium EDTA | Chelating agent | 0.1-1 |
| 8 | Phenoxyethanol | Preservative agent | 0.1-1 |
| 9 | Sodium hydroxide | Buffering agent (raise pH) | 0.1-1 |
| 10 | Hydrolyzed vegetable protein PG-propyl silanetriol | Conditioning agent | 0-0.1 |
| 11 | Polyquaternium-7 | Conditioning agent | 0-0.1 |
| 12 | Cocamidopropyl betaine | Surface active agent | 0-0.1 |
| 13 | Ethylhexylglycerin | Preservation agent | 0-0.1 |
| 14 | Styrene/VP copolymer | Opacifier | 0-0.1 |
| 15 | Cysteine HCl | Antioxidant | 0-0.1 |
| 16 | Argania spinosa kernel oil | Conditioning agent | 0-0.1 |
| 17 | PEG-35 castor oil | Surface active agent | 0-0.1 |
| 18 | Wheat amino acids | Conditioning agent | 0-0.1 |
| 19 | Hydrolyzed pea protein | Conditioning agent | 0-0.1 |
| 20 | Guaiazulene | Colorant | 0-0.1 |
| 21 | Potassium sorbate | Preservative agent | 0-0.1 |

In some embodiments, First-Product 101 may have at least one of the following properties: be a liquid and/or a solution and not an emulsion at room temperatures; have a pH of 7.3 to 7.7; be opalescent in color; not be like water; may be light sensitive; may have a scent/odor of red fruits and/or pomegranate; have a shelf-life (stability) of at least three (3) years; stored at room temperatures below eighty (80) degrees Fahrenheit; and/or be packaged in a dark glass and/or plastic bottle, such as, but not limited to a PET bottle

FIG. 2

Table 2: At least some details of Second-Product 151

| | Ingredient | Function, role, and/or purpose | Concentration (% by mass) |
|---|---|---|---|
| 1 | Water | Solvent and/or carrier | 75-100 |
| 2 | Laureth-10 | Emulsifier | 5-10 |
| 3 | Hydrogen peroxide | Oxidanting agent | 1-5 |
| 4 | Fragrance (perfume) | Fragrance (smell / odor) | 0.1-1 |
| 5 | Phosphoric acid | Buffering agent (lower pH) | 0-0.1 |
| 6 | Etidronic acid | Chelating agent | 0-0.1 |
| 7 | Styrene/VP copolymer | Opacifier | 0-0.1 |
| 8 | Argania spinosa kernel oil | Conditioning agent | 0-0.1 |
| 9 | Hydrolyzed pea protein | Conditioning agent | 0-0.1 |
| 10 | Phenoxyethanol | Preservative agent | 0-0.1 |
| 11 | Potassium sorbate | Preservative agent | 0-0.1 |

In some embodiments, Second-Product 151 may have at least one of the following properties: be a liquid and/or a solution and not an emulsion at room temperatures; have a pH of 2.4 to 3.0; be opalescent in color; not be like water; may be light sensitive; may have a scent/odor of red fruits and/or pomegranate; have a shelf-life (stability) of at least three (3) years; stored at room temperatures below eighty (80) degrees Fahrenheit; and/or be packaged in a dark glass and/or plastic bottle, such as, but not limited to a PET bottle

FIG. 3

Table 3: At least some parameters for at least some steps of method 400

| Hair Color History | Hair Type | Prep With | Cap & Heat | Reapply First-Product | Processing Time | Neutralizing Time |
|---|---|---|---|---|---|---|
| Virgin & resistant | coarse / medium | n/a | Right away | If First-Product was applied before support structure, hair looks dry or little movement in first 30 minutes of processing, then reapply | 35-45 minutes (capped & heated) | 15 minutes |
| Single process / no bleach | coarse / medium | Magic Spell | Right away | If hair looks dry or little movement in first 20 minutes of processing, then reapply | 20-35 minutes (capped & heated) | 15 minutes |
| Virgin or single process / no bleach | Fine | Magic Spell | After 10 minutes processing & little movement | If hair looks dry or little movement in first 20 minutes of processing, then reapply | 15-30 minutes | 15 minutes |
| Virgin or single process / no bleach | Baby fine | Conditioner on mids & ends | After 10 minutes processing & little movement | n/a | 10-20 minutes | 10 minutes |
| Previous bleach / Porous - Highlights or Balayage | Any hair type | Conditioner on heavily lightened areas | Do not cap or heat during process | If hair looks dry or little movement in first 20 minutes of processing, then reapply | 10-20 minutes | 10 minutes |

FIG. 5

| Color History | Hair Type | Total Surveyed | Reported Soft, Healthy Hair Post Service | Reported No Change to Hair Health Post Service | Reported a Bit of Dryness or Damage Post Service | Reported Significant Dryness or Damage Post Service |
|---|---|---|---|---|---|---|
| Virgin & Resistant | Coarse / Medium | 17 | 13 | 2 | 2 | |
| Single process, no bleach | Coarse / Medium | 12 | 10 | 1 | 1 | |
| Virgin or Single process, no bleach | Fine | 10 | 7 | 2 | | 1 |
| Virgin or Single process, no bleach | Baby fine | 3 | 2 | 1 | | |
| Previous bleach/ porous - highlights or balayage | Any hair type | 14 | 11 | 2 | 1 | |
| TOTAL | | 56 | 43 | 8 | 4 | 1 |
| % | | | 77% | 14% | 7% | 2% |

NOTES:
- 77% of clients reported their hair felt softer and healthier post Curl Cult Service
- Over 90% of clients reported no dryness or damage post Curl Cult Service

FIG. 9

COMPOSITIONS, PRODUCTS, SYSTEM, AND METHOD FOR PERMING HAIR

TECHNICAL FIELD OF THE INVENTION

The present invention relates in general to hair perming and more specifically to compositions, products, systems/kits, and methods of perming hair.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

The art and technology of creating permanent texture and curls in human hair and hairstyling has not been reinvented for decades. Many past brands and individuals have tried to reinvigorate human hair perming, but have failed to do so, lacking any true technological advances. Until the first named inventor recognized clients' desires for better human hair perming and worked diligently to solve at least three (3) of the most prevalent problems plaguing prior art human hair perming, such as: (1) damaging, harsh and unnatural results; (2) resulted in offensive fumes, smells, and odors that lingered in both the hair, skin, clothes, in the salons both during and after the prior art perming process; and (3) an outdated process that was long, messy, limiting, wasted too much water. With respect to this third problem, the prior art hair perming process was/are uncomfortable and messy, for both stylists and the clients, due in part to having to rinse out a perming solution/lotion before a later neutralizing step.

With respect to this third problem, the prior art hair perming process limited the creative freedoms of both stylists and clients as to what hair styles/shapes could be permed, because the prior art intervening rinse step meant that the physical structure for supporting the hair during the prior art hair perming process, i.e., hair perming rods (and only hair perming rods), had be robust enough to survive the aggressiveness of the prior art intervening rinse step. This limitation/restriction meant that a large diversity of other hair styles/shapes (e.g., hair twists, hair waves, and/or hair braids) could not be easily and/or effectively permed (or not permed at all) with the prior art hair perming because these other hair styles/shapes are too fragile/delicate (e.g., do not use hair perming rods) to survive the aggressiveness of the prior art intervening rinse step. Further, hair styles that have their hair style structure imparted and/or held in place by non-hair perming rods, such as, but not limited to, metal hair clips, used to create hair twists and/or waves, are made of metal and metal products are reactive to prior art hair perming chemicals (such as, prior art perming solutions that are alkaline [high pH]). With respect to this third problem, the prior art hair perming process used and uses an excess undesirable amount of water because at least two major rinses are done, the prior art intervening rinse out (to rinse out the perm solution/lotion) and a second later rinse to rinse out the prior art neutralizer.

It would be desirable to develop a new perming process that eliminates and/or reduces these at least three (3) of the most prevalent problems plaguing prior art human hair perming. It is to these ends that the present invention has been developed.

Prior art hair perming compositions, products, systems, kits, means, and/or methods tend to suffer from a number of problems, such as, but not limited to: using thioglycolic acid; using ammonia; using undesirable chemicals; using dangerous chemicals; using chemicals that excessively dry out the hair and/or skin, using chemicals that can burn the hair and/or the skin; using too many chemicals; using parabens; using sulfate surfactants; imparting undesirable chemical smells/odors to the hair, the skin, and/or to clothing; using excessive amounts of water; wasting water; using excessive heat (which can dry and/or burn the hair and/or the skin); requiring only the use of perming-rods (and not-off-the-rod tools/techniques) to allow the hair to take a new shape; taking too long; are not vegan; are not cruelty free; are complicated to use; having too many steps; sensitive stylists and/or sensitive clients/customers cannot use because of such chemicals and/or smells/odors; portions thereof; combinations thereof; and/or the like. Thioglycolic acid is the agent traditionally used in classic perms to break disulfide bonds. Thioglycolic acid is by its nature corrosive and aggressive and can therefore negatively affect hair structure.

Additionally, prior art hair perming compositions, products, systems, kits, means, and/or methods were limited to being used with perm rods such that hair that was too short to fit onto a perm rod could not be permed.

Similarly, prior art hair perming compositions, products, systems, kits, means, and/or methods do not (and cannot) provide a process to neutralize directly right on top of the perming lotion. That is, in prior art hair perming the perming lotion had to be first rinsed out entirely before the neutralizing product was added into the hair. This prior art intervening rinse step made it impossible to use off-the-rod tools/techniques (e.g., twist knots) with traditional perming. Historically, perms could not be used with off-the-rod hair setting/shaping techniques, such as, but not limited to, twist knots, braids, (finger) waves, and/or use of hair clips (e.g., two prong hair clips). Further because of this prior art intervening rinse out step, stylist artistic freedom was hampered as perms were limited to use of the perming-rods with hair rolled onto such perming-rods. Also, delicate hair shapes cannot withstand the vigorous/aggressive prior art intervening rinse out step required in prior art hair perming compositions, products, systems, kits, means, and/or methods.

Further, prior art hair perming compositions, products, systems, kits, means, and/or methods could not be safely used on color treated and/or lightened hair.

Furthermore, prior art hair perming compositions, products, systems, kits, means, and/or methods often have a harsh grow out with a visually obvious/clear demarcation in the hair of what hair was permed and what hair was not permed.

There is a need in the art for new hair perming compositions, products, systems, kits, means, and/or methods that are free of (without) one or more of these problems and/or have mitigated or reduced one or more of these problems.

It is to these ends that the present invention has been developed.

BRIEF SUMMARY OF THE INVENTION

In uniquely solving these at least three (3) of the most prevalent problems plaguing prior art human hair perming (e.g., as identified in the prior section on the "Background of the Invention"), embodiments of the present invention may: (1) reduce damage to permed hair, yielding permed hair that softer with more natural results; (2) save time, be more comfortable for the client during the perming process, and may reduce water waste; (3) be pleasant smelling with a non-lingering scent; portions thereof; combinations thereof; and/or the like. Embodiments of the present invention may utilize a first-product (first-composition) that may comprise a novel and unique combination of cysteamine HCl and cysteine HCl to soften disulphide bonds of the inner cortex layer of the hair that make up permanent hair textures. This combination of cysteamine HCl and cysteine HCl is gentler on the hair leaving the hair with little to no damage during the present inventive perming process. Additionally, PisumProtex technology comprising hydrolyzed Vegetable Protein PG-Propyl Silanetriol (Plex technology) and hydrolyzed pea protein, of the first-product (first-composition), pair up to offer strength, support, and protection to the hair during (and after) this present inventive perming process. This duo of hydrolyzed Vegetable Protein PG-Propyl Silanetriol and the hydrolyzed pea protein works to maintain elasticity and deliver moisture, shine, and softness to the hair during (and after) this present inventive perming process. This combination of first-product (first-composition) ingredients creates soft natural results, eliminating harsh lines of demarcation, and protects the hair during the chemical service from damage. Unique to embodiments of the present invention, is the permanent waving lotion, of the first-product (first-composition), that makes it a perm, to create texture in the hair; while neutralizing over top (without the prior art intervening rinse step) provides a treatment that strengthens and softens the hair all in one.

Neutralizing directly on top of the permanent waving lotion, without the prior art intervening rinse step, allows stylists to perm on traditional perm structures as well as "off rod" (or off the rod) using no structure at all or hair structures imparted/held by means other than perming rods. This no longer limits the hair texture outcomes, compromises results of extreme lengths, and cuts the entire perming process down by thirty (30) minutes or so in many instances. Clients of embodiments of the present invention remain comfortable at their service chair for 95% of the perming service, eliminating the uncomfortable and messy prior art intervening rinse out and blotting dry of perm rods halfway through a traditional (prior art) hair perming service which elevates the client's experience. Not having to rinse between the prior art perming solution and the prior art neutralizer solutions may save fifteen (15) or more gallons of water, per perm treatment; whereas, traditional (prior art) perm manufacturers would typically recommend five (5) minutes or more of rinsing in between the application of the prior art permanent waving lotion and the prior art neutralizer, then taking extra time to blot dry the hair that was just rinsed.

Embodiments of the present invention have substantially better scent, for both clients and stylists, as compared to the sulfur smelling prior art hair perms. The inventor of embodiments of the present invention spent at least two (2) years developing a scent/fragrance of a first-product (first-composition) to alleviate the unpleasant sulfur odor of past perms. Now, with respect to embodiments of the present invention, any and all perm odors dissipate once the perm is neutralized (in the novel and unique over the top fashion/manner). The client no longer smells like unpleasant chemicals when they go home; contrary to traditional (prior art) perms.

Consumers (clients) want a permanent texture solution. One that will help them minimize time styling and relying on styling tools and just "wash and go" each day for weeks or months. Unfortunately, all that has evolved in the permanent texture space are ways to remove texture, such as keratin treatments and smoothing services. Perms have traditionally been messy, smelly, and produce harsh, damage ridden results; until now, with embodiments of the present invention. Inventor(s) of embodiments of the present invention took five (5) years to develop a new clean perming system and/or process that uses a combination of cysteamine HCl and cysteine HCl to safely soften hair (disulfide) bonds and sculpt hair bonds into a new shape with soft, natural results. Packed with PisumProtex (hydrolyzed Pea Protein and hydrolyzed vegetable protein PG-propyl silanetriol [plex technology]), the present permanent hair styling system and/or process takes a fraction of the time with the revolutionary "neutralize-over-top" practice that locks the PisumProtex into the inner cortex layer of the hair as it is being reshaped, leaving the hair softer than before the perming process. Modern day stylists needed a new way to create permanent texture safely and confidently. Embodiments of the present invention's vegan, paraben free, sulfate surfactant free, and cruelty free formula and practices saves time and preserves the integrity of the hair, all the while giving clients what they truly seek: wash and go, customizable hair texture in a permanent style/shape (for weeks and/or months).

To minimize the limitations in the prior art, and to minimize other limitations that will be apparent upon reading and understanding the present specification, embodiments of the present invention describe compositions, products, systems, kits, and methods of perming (mammalian and/or human) (scalp) hair. The systems and/or the kits may comprise at least two separate products, namely, a first-product (of a first-composition [perming lotion]) and a second-product (of a second-composition [neutralizer]). The methods of use may utilize both the first-product (of the first-composition) and the second-product (of the second-composition). The first-product (first-composition) may comprise cysteamine and cysteine (and other ingredients), such that the first-product is used to break preexisting disulfide bonds in hair. The second-product (second composition) may be used to neutralize the effects of the first-product (i.e., stop the process of breaking disulfide bonds in the hair), so that new disulfide bonds in the hair may form and/or so that disulfide bonds may reform in the hair, to set the treated hair into a desired shape with desired curls, waves, texture, and/or style. The second-product (second composition) may be applied directly over the hair with the first-product, without first rinsing the hair of the first-product. Prior art hair perming processes require an intervening rinse out step, to rinse out the perming lotion before a neutralizer can be added to the hair. It is this ability to apply the second-product directly to the hair without first rinsing out the first-product that allows hair perms of the present invention to be done on hair with delicately formed shapes; that is, shaped hair that is not limited to only using perming-rods as is the case with prior art perming processes. Various on-the-rod, off-the-rod, and/or perm tools and/or perm techniques (such as, but not limited to, rods, hair clips, braids, twist knots, and/or the like) may be used to physically maintain the hair in the desired shape until the first-product and the second-product have finished acting on the hair and/or on each other. For some types of hair and/or hair color history, capping and heating may be used to help speed up the first-product action to break disulfide bonds in the hair. The Compositions, products, systems, kits, and methods of perming hair may be vegan, cruelty free, paraben free, sulfate surfactant free, use minimal water, and are without (free of) thioglycolic acid.

Note, a number of benefits arise from eliminating the prior art intervening rinse out step. With embodiments of the present invention, the second-product (second composition) may be applied directly over the hair with the first-product already mixed into the hair, without first rinsing the hair to remove the first-product. Whereas, in prior art perming processes there is the intervening rinse out step where before a neutralizer is applied to the hair, the hair is first rinsed to remove the perming lotion. That prior art intervening rinse step is absent in embodiments of the present invention. At least some of the benefits that embodiments of the present invention may have by eliminating this prior art intervening rinse out step may include: an easier perming process as compared to prior art perming processes; and/or a faster perming process (less steps in less time) as compared to prior art perming processes.

However, additional, but unexpected benefits of eliminating this prior art intervening rinse out step include the ability to now perm a vast diversity of hair shapes, using a variety of off-the-rod techniques and tools, such as, but not limited to, braids, hair twists, hair waves, and/or the like. When the prior art intervening rinse out step in included, then perming of such hair shapes is not possible because that rinse out step destroys the delicate nature of maintaining those shapes. Eliminating this prior art intervening rinse out step also provides the stylist with much greater artistic freedom as now the greater diversity of hair shapes may be permed. With the prior art intervening rinse out step eliminated, the stylist has additional and otherwise non-available options of hair shapes that may be permed.

A further, but unexpected benefit from eliminating the prior art intervening rinse out step was that now hair softening/conditioning agents may be used in the perming lotion (first-product) the hair softening benefits exist after the perming process is done, i.e., the hair softening benefits continue to exist after both the first-product and the second-product are rinses from the hair. This permits the post-perm hair to have locked in softness and a natural feel that is completely absent with prior art traditional hair perms (that include the intervening rinse out step). For example, the first-product (first-composition) may comprise a PisumProtex blend that may function/act as a hair softening agent. In some embodiments, this PisumProtex blend may comprise hydrolyzed vegetable protein PG-propyl silanetriol and hydrolyzed pea protein. After the hair perming process was complete, as taught herein, an unexpected result was obtained of the hair feeling natural and/or soft; softer than as compared the hair before the perm and/or softer as compared to how prior art hair perms leave the hair.

In some embodiments, inclusion of hydrolyzed vegetable protein PG-propyl silanetriol within the first-product (first-composition) may be referred to herein as "plex technology." In some embodiments, this plex technology helps to stabilize and/or protect amino acid bonding within hair protein during the perming process as taught herein. In some embodiments, the hydrolyzed pea protein helps to retain moisture to the hair and/or strength to the hair, during the hair perming processes and immediately thereafter. The synergistic and unique blend and/or combination of the hydrolyzed vegetable protein PG-propyl silanetriol and the hydrolyzed pea protein may be referred to as PisumProtex technology. In some embodiment, this PisumProtex blend may be locked into an inner layer of the hair once that hair is neutralized with the second-product (second-composition) without the prior art intervening rinse out step. In some embodiments, inclusion of the PisumProtex blend results in (unexpectedly) soft and hydrated hair unlike the results of any other prior art perm.

In some embodiments, a synergistic blend and/or combination of cysteamine HCl and cysteine HCl within the first-product (first-composition) may provide an effective means of breaking/preventing disulfide bonds in hair while also being gentle on the hair to permit fragile hair to be permed, such as, but not limited to, color treated and/or lightened hair. In some embodiments, the synergistic blend and/or combination of cysteamine HCl and cysteine HCl within the first-product (first-composition) may also allow/permit the prior art intervening rinse step to be completely omitted and skip from the perming process as taught herein. In some embodiments, the synergistic blend and/or combination of cysteamine HCl, cysteine HCl, hydrolyzed vegetable protein PG-propyl silanetriol, and of the hydrolyzed pea protein all within the first-product (first-composition) may also allow/permit the prior art intervening rinse step to be completely omitted and skip from the perming process as taught herein.

In some embodiments, perming hair as taught herein may result in generally healthy hair, healthier hair, soft hair, softer hair, natural feeling hair—as compared against hair that was treated with a prior art hair perming process.

It is an objective of the present invention to provide compositions, products, systems, kits, and/or methods of perming (mammalian and/or human) (scalp) hair.

It is another objective of the present invention to provide compositions, products, systems, kits, and/or methods of perming (mammalian and/or human) (scalp) hair that are safe to use.

It is another objective of the present invention to provide compositions, products, systems, kits, and/or methods of perming (mammalian and/or human) (scalp) hair that are gentler on the hair and/or on the skin as compared to prior art hair perming means.

It is another objective of the present invention to provide compositions, products, systems, kits, and/or methods of perming (mammalian and/or human) (scalp) hair that does not excessively dry the hair and/or the skin as compared to prior art hair perming means.

It is another objective of the present invention to provide compositions, products, systems, kits, and/or methods of perming (mammalian and/or human) (scalp) hair that does not burn the hair and/or the skin.

It is another objective of the present invention to provide compositions, products, systems, kits, and/or methods of perming (mammalian and/or human) (scalp) hair that are without (free of) thioglycolic acid.

It is another objective of the present invention to provide compositions, products, systems, kits, and/or methods of perming (mammalian and/or human) (scalp) hair that use significantly much less water as compared to prior art hair perming means.

It is another objective of the present invention to provide compositions, products, systems, kits, and/or methods of perming (mammalian and/or human) (scalp) hair that is/are faster than prior art hair perming means.

It is another objective of the present invention to provide compositions, products, systems, kits, and/or methods of perming (mammalian and/or human) (scalp) hair that are vegan.

It is another objective of the present invention to provide compositions, products, systems, kits, and/or methods of perming (mammalian and/or human) (scalp) hair that are cruelty free.

It is another objective of the present invention to provide compositions, products, systems, kits, and/or methods of perming (mammalian and/or human) (scalp) hair that are paraben free.

It is another objective of the present invention to provide compositions, products, systems, kits, and/or methods of perming (mammalian and/or human) (scalp) hair that are sulfate surfactant free.

It is another objective of the present invention to provide compositions, products, systems, kits, and/or methods of perming (mammalian and/or human) (scalp) hair that are ammonia free.

It is another objective of the present invention to provide compositions, products, systems, kits, and/or methods of perming (mammalian and/or human) (scalp) hair that are easy to use.

It is another objective of the present invention to provide compositions, products, systems, kits, and/or methods of perming (mammalian and/or human) (scalp) hair that uses less steps as compared to prior art hair perming means.

It is another objective of the present invention to provide compositions, products, systems, kits, and/or methods of perming (mammalian and/or human) (scalp) hair that are able to perm hair lengths and/or hair shapes previously unable to be permed.

It is another objective of the present invention to provide compositions, products, systems, kits, and/or methods of perming (mammalian and/or human) (scalp) hair that are able to perm hair without use of perm rods.

It is another objective of the present invention to provide compositions, products, systems, kits, and/or methods of perming (mammalian and/or human) (scalp) hair that are able to perm short hair that would not fit onto perm rods.

It is another objective of the present invention to provide compositions, products, systems, kits, and/or methods of perming (mammalian and/or human) (scalp) hair that are able to perm hair with on-the-rod components and/or with various off-the-rod hair setting/shaping techniques and/or components, such as, but not limited to, braids, twist knots, hair clips (e.g., two-pronged hair clips), and/or the like.

It is another objective of the present invention to provide compositions, products, systems, kits, and/or methods of perming (mammalian and/or human) (scalp) hair that are able to perm various hair shapes, including delicate shapes, such as, but not limited to, braids, twist knots, finger waves, and/or the like.

It is another objective of the present invention to provide compositions, products, systems, kits, and/or methods of perming (mammalian and/or human) (scalp) hair that use a first-product with cysteamine and cysteine and that use a second-product to neutralize the effects of the first-product, wherein the second-product is applied directly to the hair with the first-product still in the hair, without first rinsing out the first-product; wherein this allows the resulting hair perm to be done on hair with nuanced and/or delicately formed shapes.

It is another objective of the present invention to provide compositions, products, systems, kits, and/or methods of perming (mammalian and/or human) (scalp) hair that are more effective on long length hair, with margin of error significantly reduced, as compared to prior art hair perming means (which removes steps as compared against the prior art traditional perming process, and makes the perm process much faster to perm hair).

It is another objective of the present invention to provide compositions, products, systems, kits, and/or methods of perming (mammalian and/or human) (scalp) hair that sensitive stylists and/or clients/customers can use (i.e., sensitive to chemicals and/or chemical smells).

It is another objective of the present invention to provide compositions, products, systems, kits, and/or methods of perming (mammalian and/or human) (scalp) hair that may be utilized on lightened hair and/or on artificially colored hair.

It is another objective of the present invention to provide compositions, products, systems, kits, and/or methods of perming (mammalian and/or human) (scalp) hair that may have a softer grow out with no to minimal demarcations between the permed hair and the unpermed hair.

It is another objective of the present invention to provide compositions, products, systems, kits, and/or methods of perming (mammalian and/or human) (scalp) hair that does not leave the permed hair smelling of chemicals.

It is another objective of the present invention to provide compositions, products, systems, kits, and/or methods of perming (mammalian and/or human) (scalp) hair that is a simpler, safer, and more compelling approach to perming.

It is another objective of the present invention to be able to use metal tools and/or metal products, such as, but not limited to, metal hair clips, with perming solutions and/or neutralizing solutions.

It is yet another objective of the present invention to provide compositions, products, systems, kits, and/or methods of perming (mammalian and/or human) (scalp) hair that holds up well for weeks or months, but less than one year, after use.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 2 depicts Table 1 which may show and/or include at least some information and/or details of the first-product (first-composition).

FIG. 3 depicts Table 2 which may show and/or include at least some information and/or details of the second-product (second-composition).

FIG. 5 depicts Table 3 which may depict at least some information/details pertaining to at least some of the steps of the method of FIG. 4.

FIG. 9 depicts a Table 4 that displays data with respect to a customer/client survey of hair softness, health, and/or damage before and after perming pursuant to a hair perming method discussed in FIG. 4.

Figure 1:
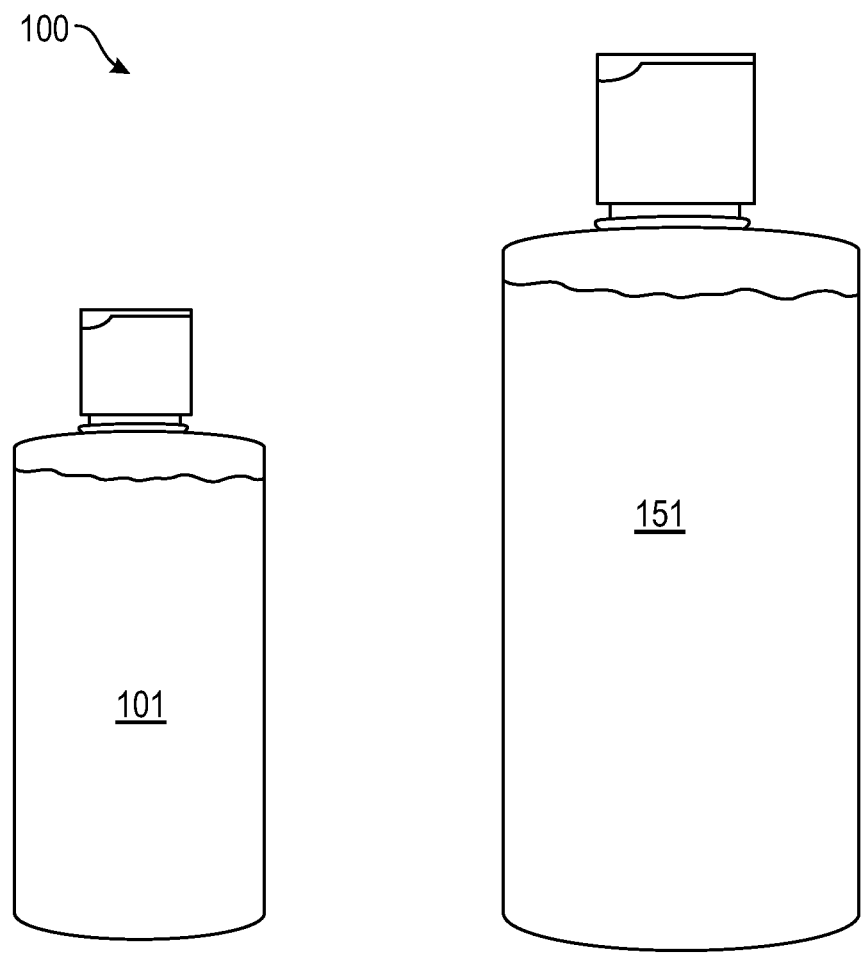
FIG. 1 shows a block diagram of a kit and/or of a system that may comprise at least two separate/distinct products, namely a first-product (first-composition) and a second-product (second-composition), that may be used to "perm" mammalian and/or human hair, such as, but not limited to, hair of the scalp or some portion thereof.

REFERENCE NUMERAL SCHEDULE 100 system/kit for perming hair 100
101 first-product 101
151 second-product 151
400 method of perming hair 400
401 step of prepping hair 401
403 step of setting/establishing shape of hair 403
405 step of applying first-product to hair 405
407 step of re-applying first-product to hair, if triggered 407
409 step of processing hair with first-product 409
411 step of capping and heating hair with first-product 411
413 step of performing/executing elasticity test on hair 413
415 step of applying second-product to hair with first-product 415
417 step of checking shape of hair 417
419 step of neutralizing first-product and regenerating disulfide bonds 419
421 step of removing support-structures from hair and/or undoing off-the-rod 421
423 step of rinsing the hair 423
425 step of conditioning the hair 425
427 step of styling the hair 427
429 step of re-shaping hair with first-product & waiting before redoing elasticity test 429
601 drawing of prepping hair 601
602 hair (human hair or mammalian hair) 602
603 drawing of rolling rods (support-structures) onto hair 603
604 rod (perming-rod) 604
605 drawing of applying first-product to hair 605
607 drawing of allowing hair to process with first-product 607
608a hair/scalp (processing) bag/cap 608a
608b heater (for hair) 608b
609 drawing of portion of elasticity test 609
611 drawing applying second-product to first-product and to hair 611
613 drawing of removing rods (support-structures) from hair 613
615 drawing of rinsing both first-product and second-product from hair 615
617 drawing of condition hair 617
701 left-side drawing (hair strand(s) under tension) 701
703 right-side drawing (hair strand(s) relaxed) 703
705 hair strand(s) 705
821 off-the-rod setting technique of hair clips and/or hair twists 821
822 (metal) hair clip 822
823 off-the-rod setting technique of hair twists 823
825 off-the-rod setting technique of hair clips 825
827 off-the-rod setting technique of braids 827

DETAILED DESCRIPTION OF THE INVENTION

Compositions, products, systems, kits, and/or methods of perming hair are disclosed and discussed herein. Hair in this context may refer to mammalian (including human) hair and/or hair that typically grows from the scalp of a mammalian head, i.e., hair that is usually at least mostly (substantially) naturally constructed from the protein keratin.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

FIG. 1 shows a block diagram of a kit 100 and/or a system 100 that may comprise at least two products that may be used to "perm" mammalian and/or human hair, such as, but not limited to, hair of the scalp or some portion thereof. In some embodiments, a hair "perm" may be short for a "permanent" or a "permanent wave" and may consist of establishing and/or setting waves, curls, and/or the like in the hair that may last for weeks or months, but less than one (1) year. Prior art perms may be applied using thermal or chemical means (e.g., thioglycolic acid). People with generally straight hair may at times desire to have curly or waving hair, and getting a perm may be an ideal and/or efficient means of obtaining curly or waving hair, wherein the curls or the waves do not have to be established on a daily basis as the permed hair will maintain the curls or the waves for weeks or months. Additionally, people with naturally curly or wavy hair may also get perms to establish curls or waves of different shapes, tightness, textures, and/or styles from the preexisting natural curls or waves. Chemically in the hair perm process preexisting disulfide bonds in the proteins of the hair may be broken and then reformed to form curls and/or waves of desired shapes, tightness, textures, and/or styles. In some embodiments, these at least two products of the kit/system 100 may be designated first-product 101 and second-product 151.

Continuing discussing FIG. 1 in some embodiments, sizing of first-product 101 and/or of second-product 151 are not intended to be conveyed by the shapes and/or sizes shown in FIG. 1. However, with respect to intended use of first-product 101 and of second-product 151, in some embodiments, the volume and/or the amount of second-product 151 applied to the hair may be from 1.5 times to two (2) times the volume/amount of first-product 101 used on the hair. As such, second-product 151 may be available in a size/volume that is larger than the available size/volume of first-product 101. For example, and without limiting the scope of the present invention, when first-product 101 may be available in a size/volume of 500 mL (milliliter), then second-product 151 may be available in a size/volume of 1,000 mL (i.e., of one [1] liter [L]).

FIG. 2 may depict Table 1 which may show and/or include at least some information and/or details of first-product 101. In some embodiments, first-product 101 may be a liquid solution at room temperatures that may comprise: water, cysteamine HCl, PEG-40 hydrogenated castor oil, polysorbate 20, fragrance (perfume and/or parfum), imidazolidinyl urea, tetrasodium EDTA, phenoxyethanol, and sodium hydroxide (NaOH). In some embodiments, first-product 101 may further/additionally comprise one or more of: hydrolyzed vegetable protein PG-propyl silanetriol, polyquaternium-7, cocamidopropyl betaine, ethylhexylglycerin, styrene/VP copolymer, cysteine HCl, *Argania spinosa* kernel oil, PEG-35 castor oil, wheat amino acids, hydrolyzed pea protein, guaiazulene, and/or potassium sorbate.

Note, HCl may be an abbreviation for hydrochloric acid. Note, EDTA may be an abbreviation for ethylenediamine tetraacetic acid. Note, PEG may be an abbreviation for polyethylene glycol.

Continuing discussing FIG. 2, in some embodiments, the water of first-product 101 may function at least as a solvent and/or as a carrier. In some embodiments, the cysteamine HCl of first-product 101 may function at least as a hair waving agent. In some embodiments, cysteamine HCl may act on hair by breaking preexisting disulfide bonds in the hair that is in direct physical contact with cysteamine HCl. In some embodiments, the PEG-40 hydrogenated castor oil of first-product 101 may function at least as a surface active agent. In some embodiments, the polysorbate 20 of first-product 101 may function at least as a surface active agent. In some embodiments, the fragrance (perfume) of first-product 101 may function to at least provide a predetermined and desired smell/odor of first-product 101. In some embodiments, the fragrance (perfume) of first-product 101 may be at least one (1) predetermined fragrances, perfumes, essential oils, botanical extracts, and/or the like. In some embodiments, the imidazolidinyl urea of first-product 101 may function at least as a preservative agent. In some embodiments, the tetrasodium EDTA of first-product 101 may function at least as a chelating agent. In some embodiments, the phenoxyethanol of first-product 101 may function at least as a preservative agent. In some embodiments, the sodium hydroxide of first-product 101 may function at least as a (pH) buffering agent (pH raising agent). In some embodiments, the hydrolyzed vegetable protein PG-propyl silanetriol, polyquaternium-7 of first-product 101 may function at least as a conditioning agent. In some embodiments, the polyquaternium-7 of first-product 101 may function at least as a conditioning agent. In some embodiments, the cocamidopropyl betaine of first-product 101 may function at least as a surface-active agent. In some embodiments, the ethylhexylglycerin of first-product 101 may function at least as a preservative agent. In some embodiments, the styrene/VP copolymer of first-product 101 may function at least as an opacifier (e.g., to help first-product 101 to be at least substantially [mostly] human visually opaque). In some embodiments, the cysteine HCl of first-product 101 may function at least as an antioxidant. In some embodiments, the *Argania spinosa* kernel oil of first-product 101 may function at least as a conditioning agent. In some embodiments, the PEG-35 castor oil of first-product 101 may function at least as a surface-active agent. In some embodiments, the wheat amino acids of first-product 101 may function at least as a conditioning agent. In some embodiments, the hydrolyzed pea protein of first-product 101 may function at least as a conditioning agent. In some embodiments, the guaiazulene of first-product 101 may function at least as a colorant. In some embodiments, the potassium sorbate of first-product 101 may function at least as a preservative agent.

Continuing discussing FIG. 2, in some embodiments, the water of first-product 101 may be present in a concentration range of 75% to 97%, by mass. In some embodiments, the water of first-product 101 may be present in a concentration range of 79.8% to 96.6%, by mass. In some embodiments, the cysteamine HCl of first-product 101 may be present in a concentration range of five (5) % to ten (10) % by mass. In some embodiments, the PEG-40 hydrogenated castor oil of first-product 101 maybe present in a concentration range of one (1) % to five (5) % by mass. In some embodiments, the polysorbate 20 of first-product 101 may be present in a concentration range of one (1) % to five (5) % by mass. In some embodiments, the fragrance (perfume) of first-product 101 may be present in a concentration range of one (1) % to five (5) % by mass. In some embodiments, the imidazolidinyl urea of first-product 101 may be present in a concentration range of 0.1% to one (1) % by mass. In some embodiments, the tetrasodium EDTA of first-product 101 may be present in a concentration range of 0.1% to one (1) % by mass. In some embodiments, the phenoxyethanol of first-product 101 may be present in a concentration range of 0.1% to one (1) % by mass. In some embodiments, the sodium hydroxide of first-product 101 may be present in a concentration range of 0.1% to one (1) % by mass. In some embodiments, the hydrolyzed vegetable protein PG-propyl silanetriol of first-product 101 may be present in a concentration range of zero (0) % to 0.1% by mass. In some embodiments, the polyquaternium-7 of first-product 101 may be present in a concentration range of zero (0) % to 0.1% by mass. In some embodiments, the cocamidopropyl betaine of first-product 101 may be present in a concentration range of zero (0) % to 0.1% by mass. In some embodiments, the ethylhexylglycerin of first-product 101 may be present in a concentration range of zero (0) % to 0.1% by mass. In some embodiments, the styrene/VP copolymer of first-product 101 may be present in a concentration range of zero (0) % to 0.1% by mass. In some embodiments, the cysteine HCl of first-product 101 may be present in a concentration range of zero (0) % to 0.1% by mass. In some embodiments, the *Argania spinosa* kernel oil of first-product 101 may be present in a concentration range of zero (0) % to 0.1% by mass. In some embodiments, the PEG-35 castor oil of first-product 101 may be present in a concentration range of zero (0) % to 0.1% by mass. In some embodiments, the wheat amino acids of first-product 101 may be present in a concentration range of zero (0) % to 0.1% by mass. In some embodiments, the hydrolyzed pea protein of first-product 101 may be present in a concentration range of zero (0) % to 0.1% by mass. In some embodiments, the guaiazulene of first-product 101 may be present in a concentration range of zero (0) % to 0.1% by mass. In some embodiments, the potassium sorbate of first-product 101 may be present in a concentration range of zero (0) % to 0.1% by mass. In some embodiments, ingredient concentration of first-product 101 may be framed in percent (%) by volume instead of % by mass.

Continuing discussing FIG. 2, in some embodiments, first-product 101 may have at least one of the following properties: be a liquid and/or a solution and not an emulsion at room temperatures; have a pH of 7.3 to 7.7; be opalescent in color; be opaque; not be clear like water; may be light sensitive; may have a scent/odor of red fruits and/or pomegranate; have a shelf-life (stability) of at least three (3) years; may be stored at room temperatures below eighty (80) degrees Fahrenheit and above freezing; and/or be packaged in a dark glass and/or a dark plastic bottle, such as, but not limited to a PET (polyethylene terephthalate) bottle.

Continuing discussing FIG. 2, in some embodiments, this pH of 7.3 to 7.7 for first-product 101 may be a generally neutral and non-alkaline pH (and non-acidic pH). In some embodiments, this pH of 7.3 to 7.7 for first-product 101 may contribute to first-product 101 being compatible with making direct physical contact with various metals and/or metal alloys, such as those typical of metal hair-clips 822. See e.g., FIG. 8A and/or FIG. 8C for metal hair-clips 822. Prior art perming solutions and/or prior art neutralizers are more alkaline and are not compatible for direct physical contact with metals and/or metal alloys, such as those with metal hair-clips 822.

Cysteamine is a derivative of cysteine, a natural component of the hair structure. The function performed by the cysteamine in first-product 101 may be at least mostly (substantially) similar to that of thioglycolic acid of prior art hair perming means; however, the action of the cysteamine is by far less aggressive. Cysteamine operates along with cysteine and the complex of the vegetable amino acids (e.g., the hydrolyzed vegetable protein PG-propyl silanetriol, the wheat amino acids, and the hydrolyzed pea protein) which recall the hair structure and the hair's composition. Thanks to the affinity with the hair structure, cysteamine, cysteine, and the complex of the vegetable amino acids allow natural hair movement. Gradually and gently the cysteamine, cysteine, and the complex of the vegetable amino acids modify the keratin structure of the hair. The amino acids bind to the free SH groups and generate new bonds in the hair. Note, the oxygen (e.g., oxidating agent) of the neutralizer (second-product 151) stabilizes these bonds.

Continuing discussing FIG. 2, in some embodiments, a synergistic blend and/or combination of cysteamine HCl and cysteine HCl within the first-product 101 (first-composition 101) may provide an effective means of breaking/preventing disulfide bonds in hair while also being gentle on the hair to permit fragile hair to be permed, such as, but not limited to, color treated and/or lightened hair. In some embodiments, the synergistic blend and/or combination of cysteamine HCl and cysteine HCl within the first-product 101 (first-composition 101) may also allow/permit the prior art intervening rinse step to be completely omitted and skip from the perming process as taught herein.

Continuing discussing FIG. 2, in some embodiments, inclusion of hydrolyzed vegetable protein PG-propyl silanetriol within the first-product 101 (first-composition 101) may be referred to herein as "plex technology." In some embodiments, this plex technology helps to stabilize and/or protect amino acid bonding within hair protein during the perming process as taught herein. In some embodiments, the hydrolyzed pea protein helps to retain moisture to the hair and/or strength to the hair, during the hair perming processes and immediately thereafter. The synergistic and unique blend and/or combination of the hydrolyzed vegetable protein PG-propyl silanetriol and the hydrolyzed pea protein may be referred to as PisumProtex technology. In some embodiment, this PisumProtex blend may be locked into an inner layer of the hair once that hair is neutralized with the second-product 151 (second-composition 151) without the prior art intervening rinse out step. In some embodiments, inclusion of the PisumProtex blend results in (unexpectedly) soft and hydrated hair unlike the results of any other prior art perm.

Continuing discussing FIG. 2, in some embodiments, first-product 101 may be termed a composition 101 and/or a first-composition 101. In some embodiments, this composition 101 may be used to break at least some preexisting disulfide bonds in mammalian hair. In some embodiments, this composition 101 may comprise water and cysteamine HCl, wherein this composition 101 may be used in a method of perming at least some of the mammalian hair (such as, but not limited to, method 400). In some embodiments, this composition 101 may comprise water, cysteamine HCl, and cysteine HCl. In some embodiments, the cysteamine HCl present in this composition 101 may be present at a concentration range of five (5) percent (%) to ten (10) percent (%), by mass. In some embodiments, this composition 101 may further comprise PEG-40 hydrogenated castor oil, polysorbate 20, a fragrance, imidazolidinyl urea, tetrasodium EDTA, phenoxyethanol, and sodium hydroxide. In some embodiments, this composition 101 may further comprise one or more of: hydrolyzed vegetable protein PG-propyl silanetriol, polyquaternium-7, cocamidopropyl betaine, ethylhexylglycerin, styrene/VP copolymer, cysteine HCl, *Argania spinosa* kernel oil, PEG-35 castor oil, wheat amino acids, hydrolyzed pea protein, guaiazulene, and/or potassium sorbate. See e.g., FIG. 2.

FIG. 3 may depict Table 2 which may show and/or include at least some information and/or details of second-product 151. In some embodiments, second-product 151 may be a liquid solution at room temperatures that may comprise: water, Laureth-10, hydrogen peroxide, and at least one fragrance/perfume (parfum). In some embodiments, second-product 151 may further/additionally comprise one or more of: phosphoric acid, etidronic acid, styrene/VP copolymer, *Argania spinosa* kernel oil, hydrolyzed pea protein, phenoxyethanol, and/or potassium sorbate.

Continuing discussing FIG. 3, in some embodiments, the water of second-product 151 may function at least as a solvent and/or as a carrier. In some embodiments, the Laureth-10 of second-product 151 may function at least as an emulsifier. In some embodiments, the Laureth-10 of second-product 151 may to help the fragrance(s) combine into the solution of second-product 151 and not separate out from this solution. In some embodiments, the hydrogen peroxide of second-product 151 may function at least as an oxidating agent. In some embodiments, the fragrance (perfume and/or parfum) of second-product 151 may function to at least provide a predetermined and desired smell/odor of second-product 151. In some embodiments, the fragrance (perfume and/or parfum) of second-product 151 may be at least one (1) predetermined fragrances, perfumes, parfums, essential oils, botanical extracts, and/or the like. In some embodiments, the fragrance (perfume and/or parfum) of second-product 151 may be the same or different as the fragrance (perfume and/or parfum) of first-product 101. In some embodiments, the phosphoric acid of second-product 151 may function to at least as a (pH) buffering agent (e.g., as a pH lowering agent). In some embodiments, the etidronic acid of second-product 151 may function at least as a chelating agent. In some embodiments, the styrene/VP copolymer of second-product 151 may function at least as an opacifier. In some embodiments, the *Argania spinosa* kernel oil of second-product 151 may function at least as a conditioning agent. In some embodiments, the hydrolyzed pea protein of second-product 151 may function at least as a conditioning agent. In some embodiments, the phenoxyethanol of second-product 151 may function at least as a preservative agent. In some embodiments, the potassium sorbate of second-product 151 may function at least as a preservative agent.

Continuing discussing FIG. 3, in some embodiments, the water of second-product 151 may be present in a concentration range of 75% to 94%, by mass. In some embodiments, the water of second-product 151 may be present in a concentration range of 83.3% to 93.9%, by mass. In some embodiments, the Laureth-10 of second-product 151 may be present in a concentration range of five (5) % to ten (10) % by mass. In some embodiments, the hydrogen peroxide of second-product 151 maybe present in a concentration range of one (1) % to five (5) % by mass. In some embodiments, the fragrance (perfume) of second-product 151 may be present in a concentration range of 0.1% to one (1) % by mass. In some embodiments, the phosphoric acid of second-product 151 may be present in a concentration range of zero (0) % to 0.1% by mass. In some embodiments, the etidronic acid of second-product 151 may be present in a concentration range of zero (0) % to 0.1% by mass. In some embodiments, the styrene-NP copolymer of second-product 151 may be present in a concentration range of zero (0) % to 0.1% by mass. In some embodiments, the *Argania spinosa* kernel oil of second-product 151 may be present in a concentration range of zero (0) % to 0.1% by mass. In some embodiments, the hydrolyzed pea protein of second-product 151 may be present in a concentration range of zero (0) % to 0.1% by mass. In some embodiments, the phenoxyethanol of second-product 151 may be present in a concentration range of zero (0) % to 0.1% by mass. In some embodiments, the potassium sorbate of second-product 151 may be present in a concentration range of zero (0) % to 0.1% by mass. In some embodiments, ingredient concentration of second-product 151 may be framed in percent (%) by volume instead of % by mass.

Continuing discussing FIG. 3, in some embodiments, second-product 151 may have at least one of the following properties: be a liquid and/or a solution and not an emulsion at room temperatures; have a pH of 2.4 to 3.0; be opalescent in color; not be clear like water; be opaque; may be light sensitive; may have a scent/odor of red fruits and/or pomegranate; have a shelf-life (stability) of at least three (3) years; may be stored at room temperatures below eighty (80) degrees Fahrenheit and above freezing; and/or be packaged in a dark glass and/or a dark plastic bottle, such as, but not limited to a PET bottle.

Continuing discussing FIG. 3, in some embodiments, second-product 151 may be termed a second-composition. In some embodiments, this second-composition may be used to neutralize the first-composition (first-product 101). In some embodiments, this neutralization of first-product 101 may be with respect to the second-composition 151 at least mostly (substantially) stopping the first-composition as breaking (and/or preventing) disulfide bonds in hair (e.g., in mammalian hair). In some embodiments, this second-composition 151 may comprise water, Laureth-10, hydrogen peroxide, and a fragrance. In some embodiments, this second-composition 151 may have a pH of 2.4 to 3.0. In some embodiments, this second-composition 151 may further comprise one or more of: phosphoric acid, etidronic acid, styrene/VP copolymer, *Argania spinosa* kernel oil, hydrolyzed pea protein, phenoxyethanol, and/or potassium sorbate. See e.g., FIG. 3.

In some embodiments, first-product 101 and/or second-product 151 may comprise "plex technology"; wherein plex technology as used herein may comprise one or more hydrolyzed plant and/or vegetable proteins and/or amino acids, such as, but not limited to: hydrolyzed vegetable protein PG-propyl silanetriol, wheat amino acids, hydrolyzed pea protein, portions thereof, combinations thereof, and/or the like. In some embodiments, this plex technology protects the bonds in the hair as the hair perming process progresses. In some embodiments, this plex technology protects the new and/or reformed disulfide bonds in the hair as the hair perming process progresses.

At least some embodiments of the present invention may be characterized as a system and/or as a kit for perming mammalian hair, wherein such a system/kit may comprise the first-composition (first-product 101) and the second-composition (second-product 151). In some embodiments, the first-composition (first-product 101) and the second-composition (second-product 151) may be kept, stored, and/or maintained separate from each other, until used together pursuant to a method of perming mammalian hair (such as, but not limited to, method 400). See e.g., FIG. 1, FIG. 2, and FIG. 3.

Figure 4:
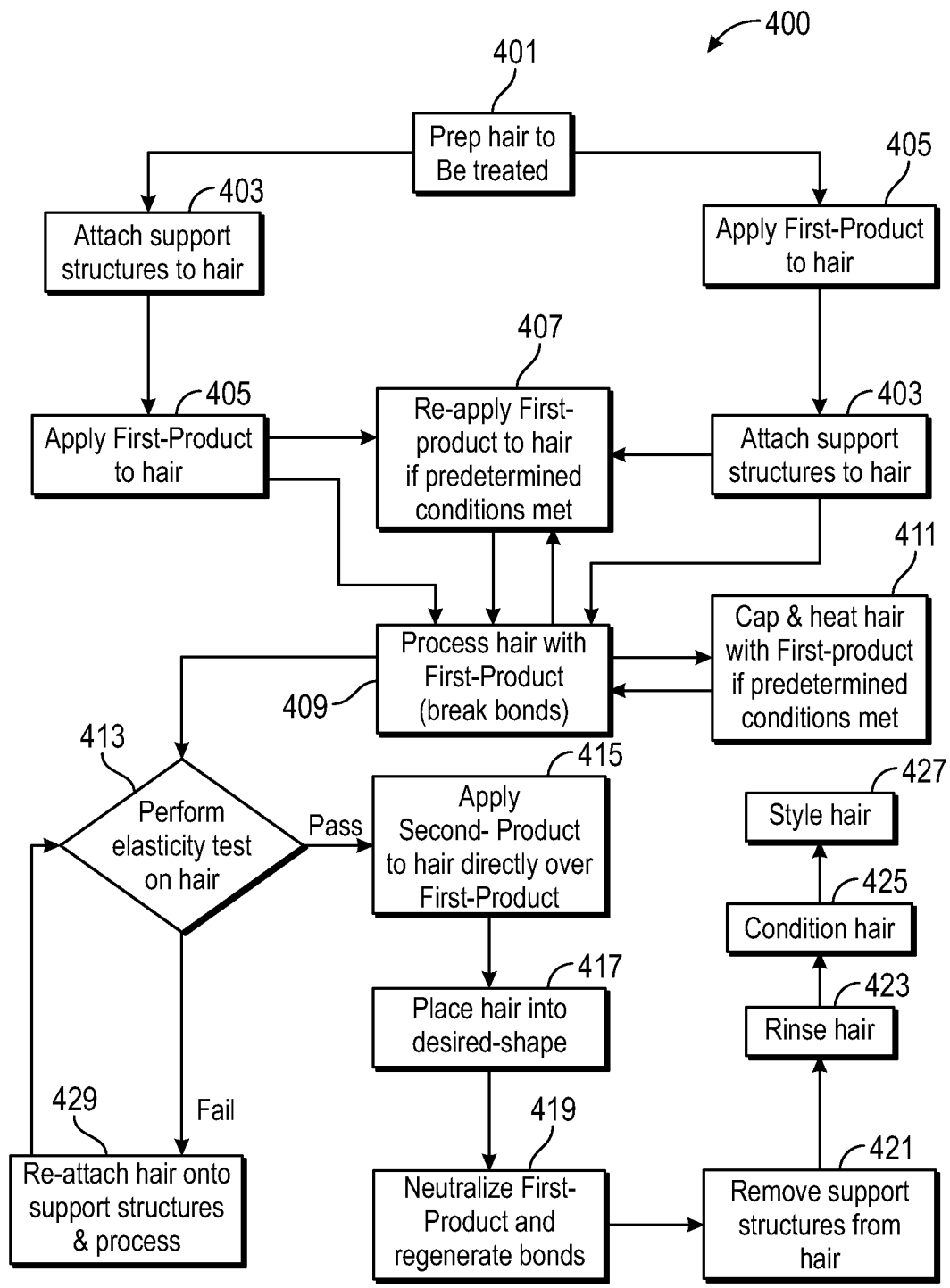
FIG. 4 depicts a flow diagram of a method to perm hair (e.g., method 400).
Figure 6A:
FIG. 6A shows a drawing of prepping hair that may be applicable and/or representative of prepping step 401 of method 400.
Figure 6B:
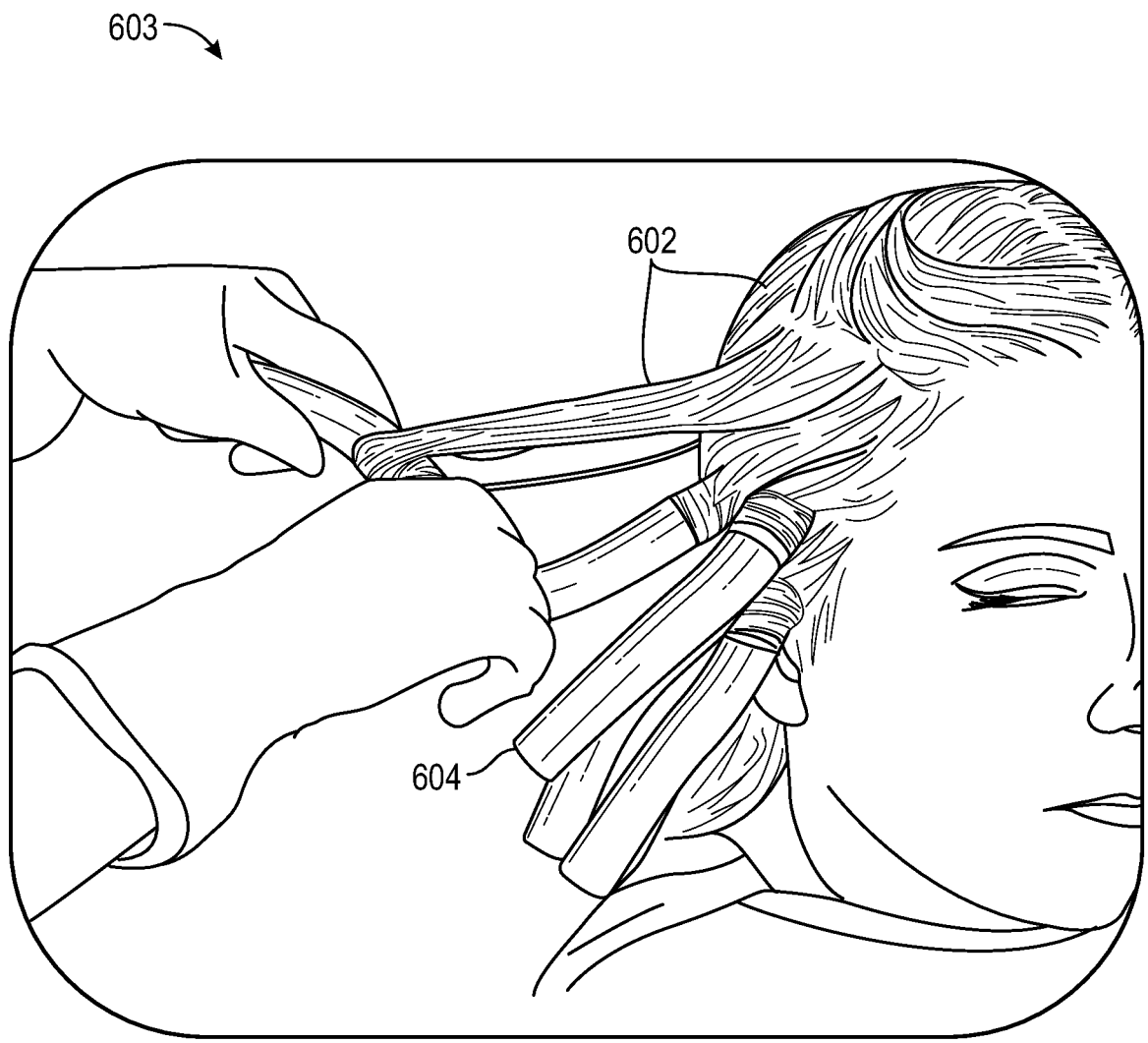
FIG. 6B shows a drawing of rolling rods (support-structures) onto hair that may be applicable and/or representative of step 403 of method 400.
Figure 6C:
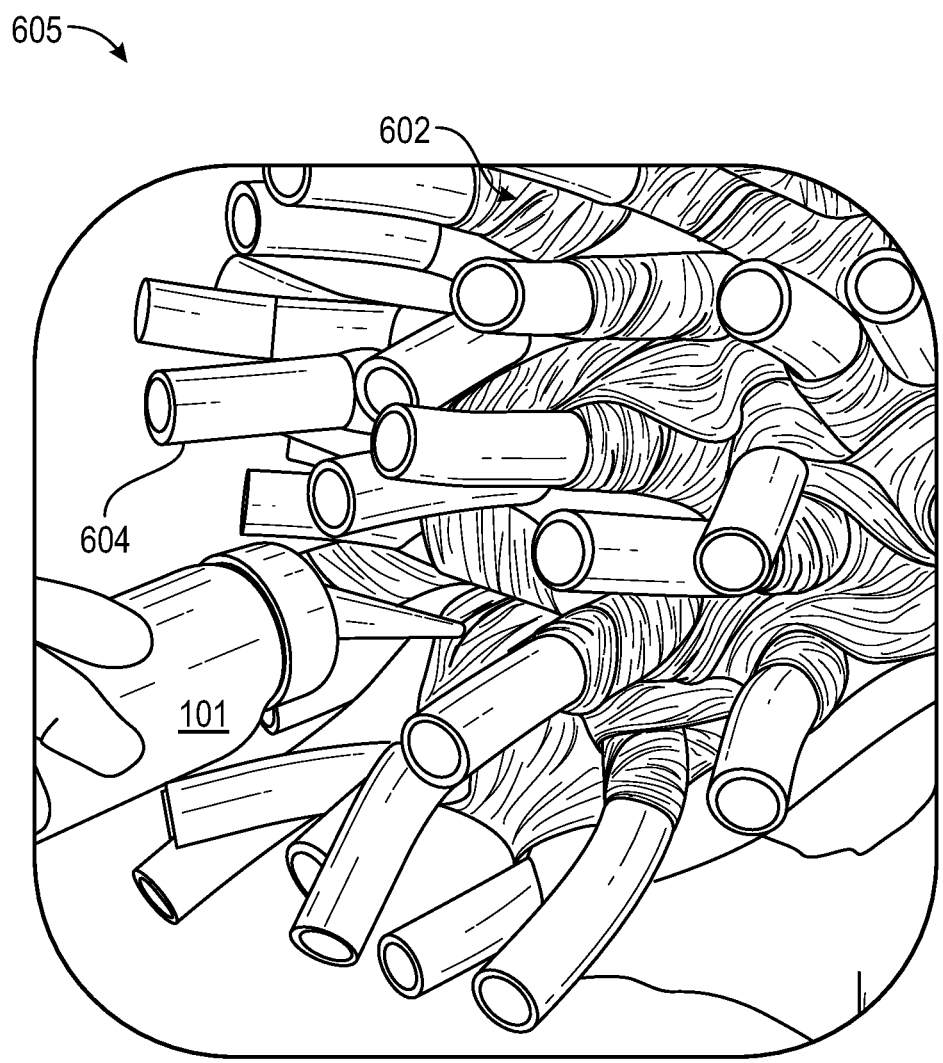
FIG. 6C shows a drawing of applying the first-product to hair that may be applicable and/or representative of step 405 of method 400.
Figure 6D:
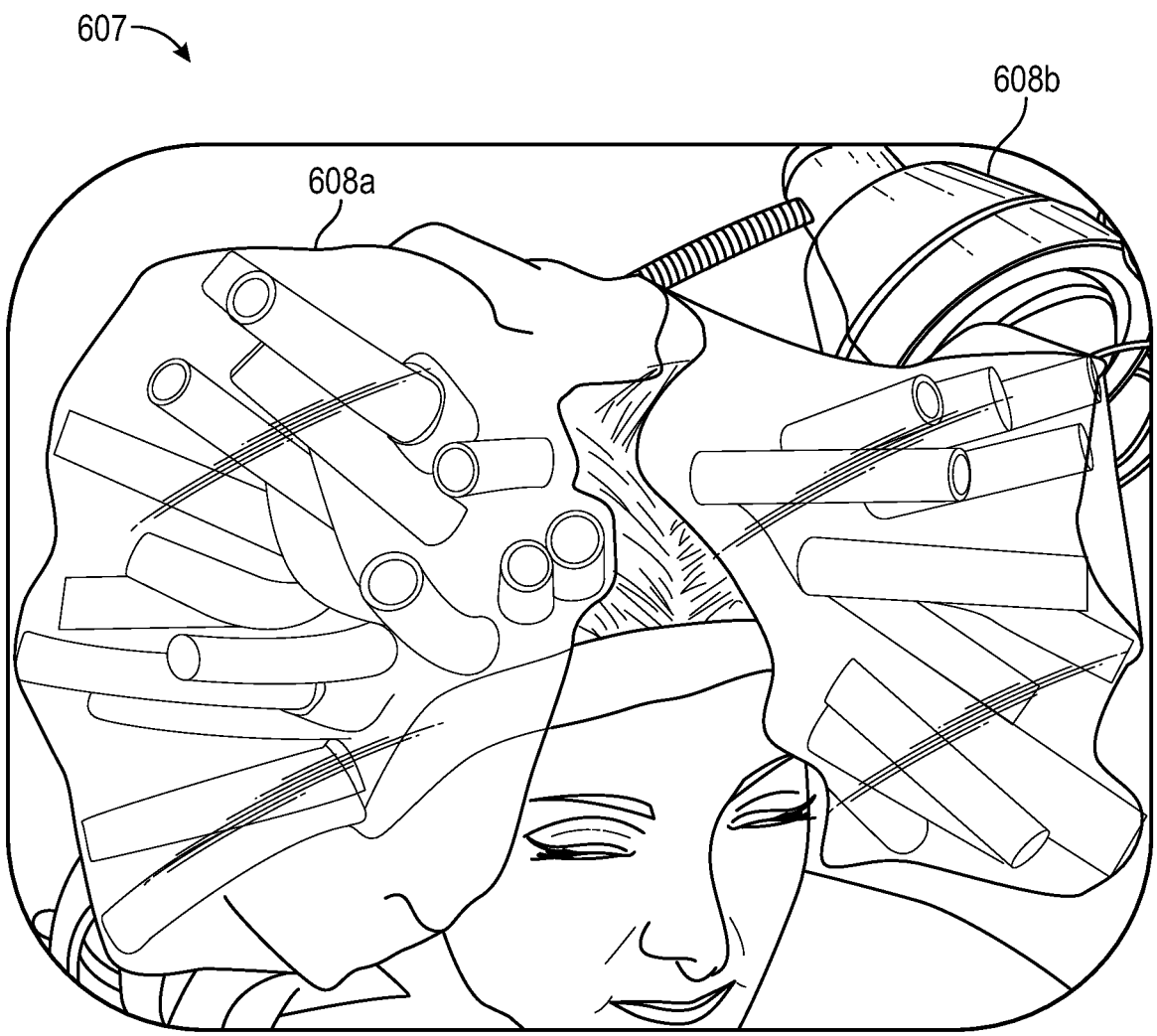
FIG. 6D shows a drawing of allowing the hair to process with first-product that may be applicable and/or representative of step 409 and/or of step 411 of method 400.
Figure 6E:
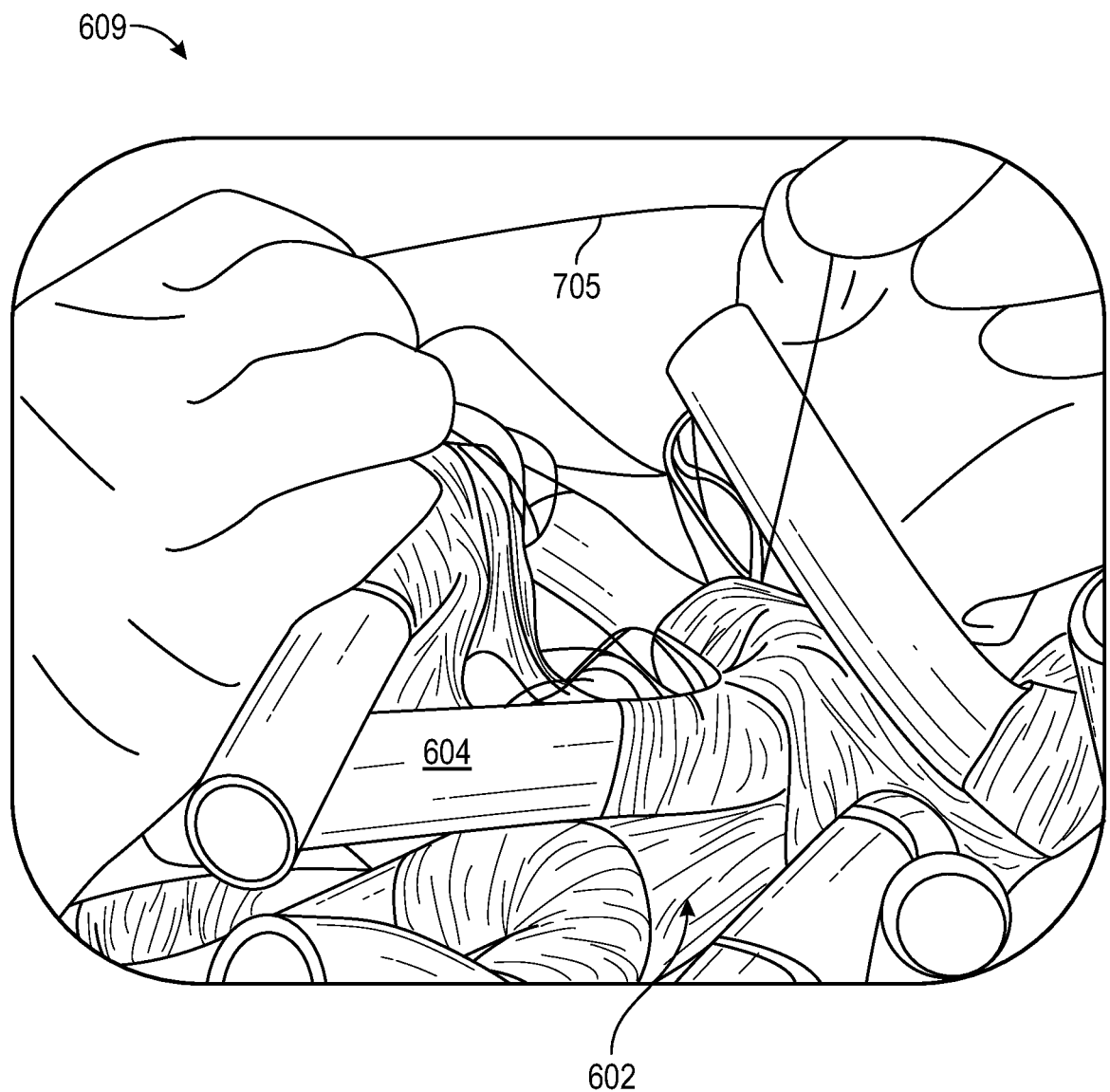
FIG. 6E shows a drawing of at least a portion of an elasticity test of hair strand(s) that may be applicable and/or representative of step 413 (elasticity test) of method 400.
Figure 6F:
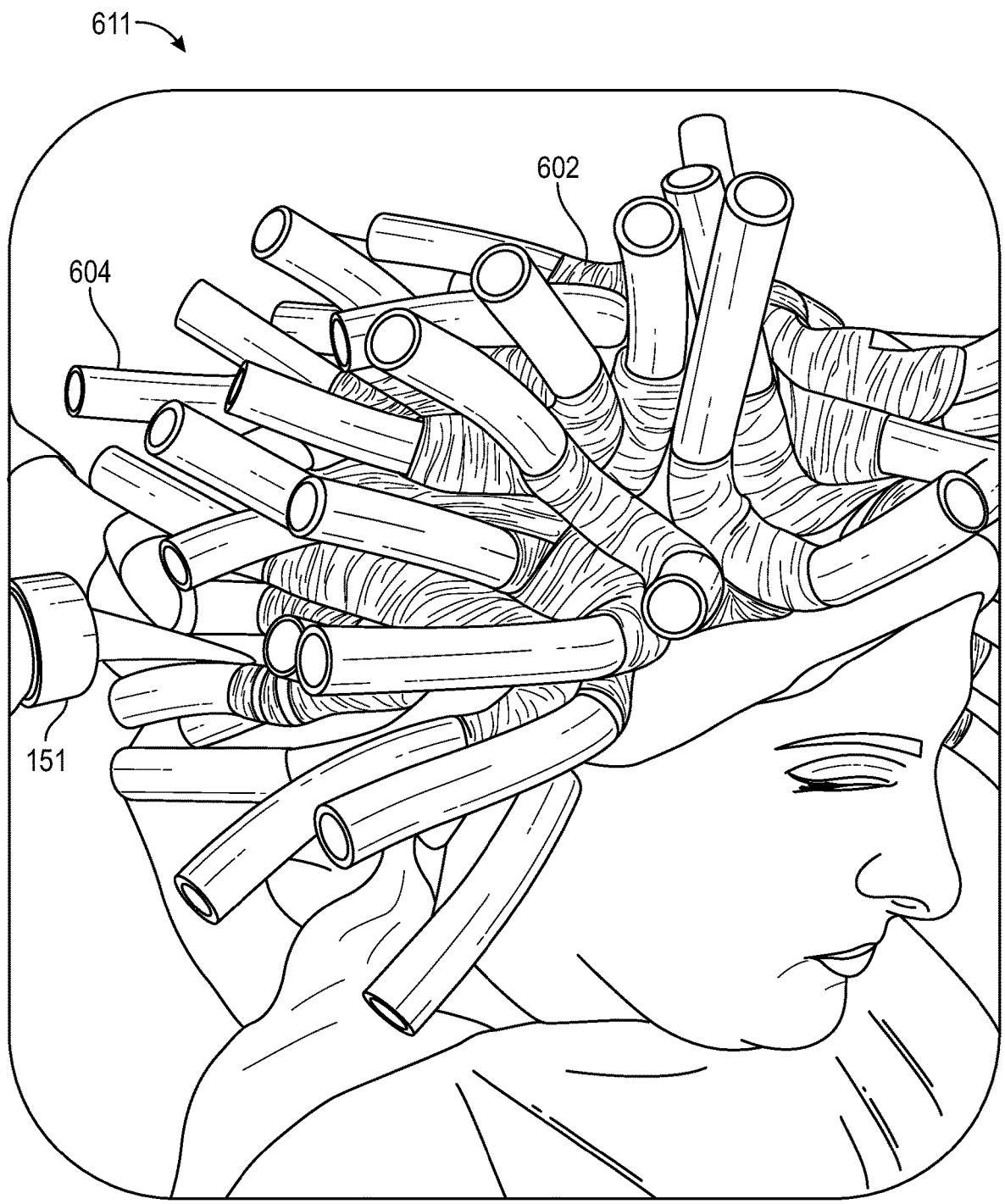
FIG. 6F shows a drawing applying the second-product to the first-product and to the hair that may be applicable and/or representative of step 415, step 417, and/or of step 419 of method 400.
Figure 6G:
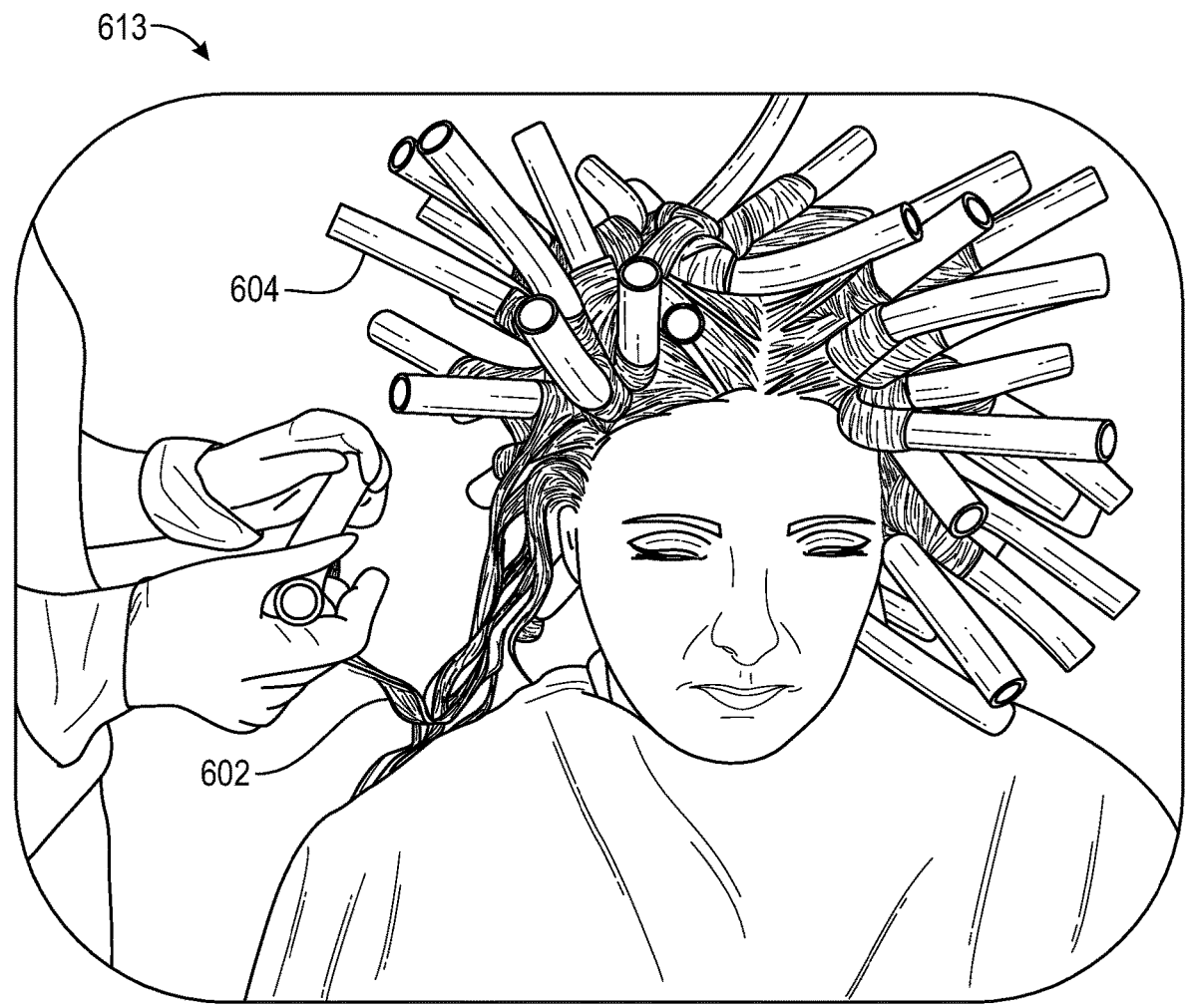
FIG. 6G shows a drawing of removing the rods (support-structures) from the hair that may be applicable and/or representative of step 421 of method 400.
Figure 6H:
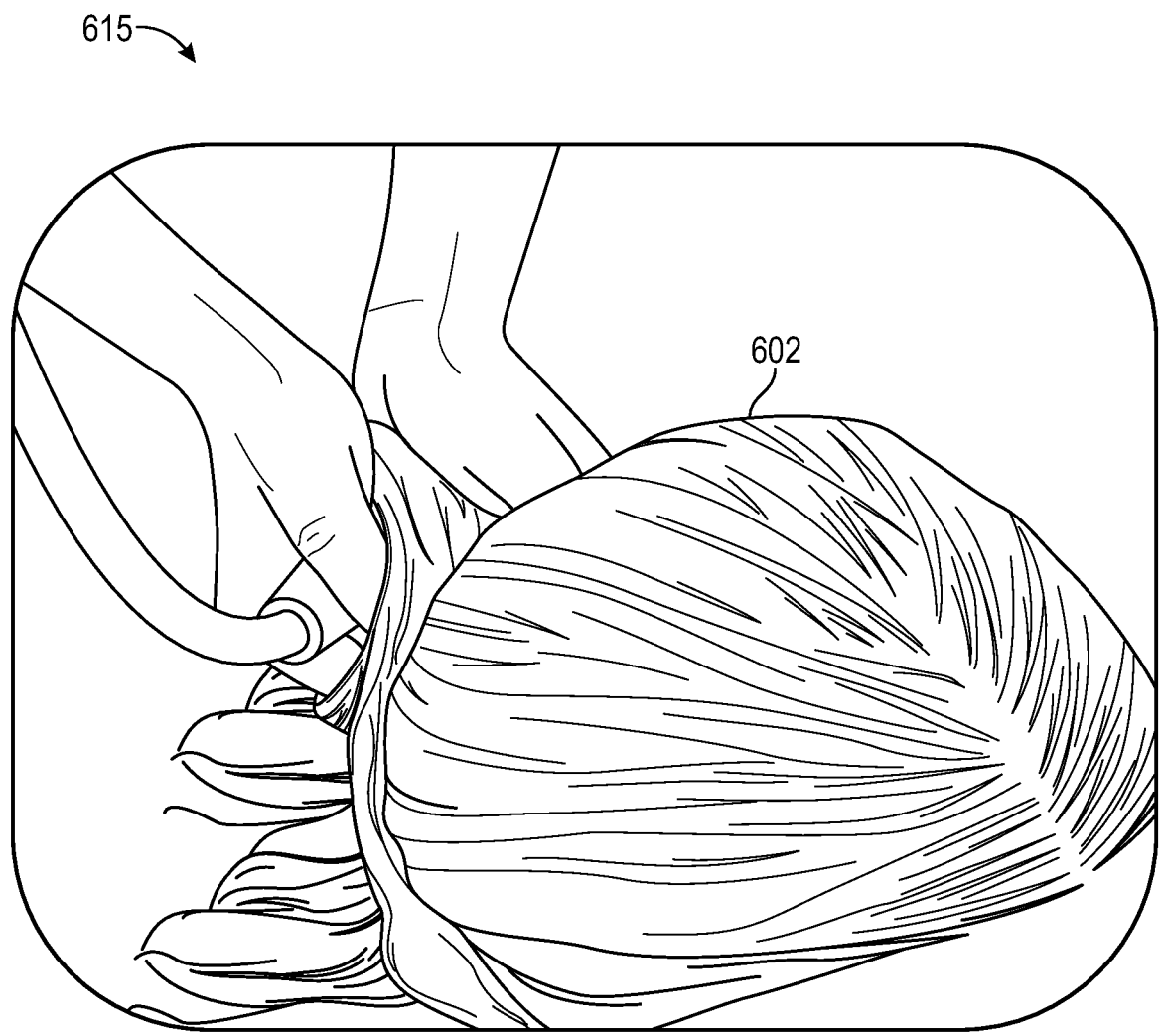
FIG. 6H shows a drawing of rinsing both the first-product and the second-product from the hair that may be applicable and/or representative of step 423 of method 400.
Figure 6I:
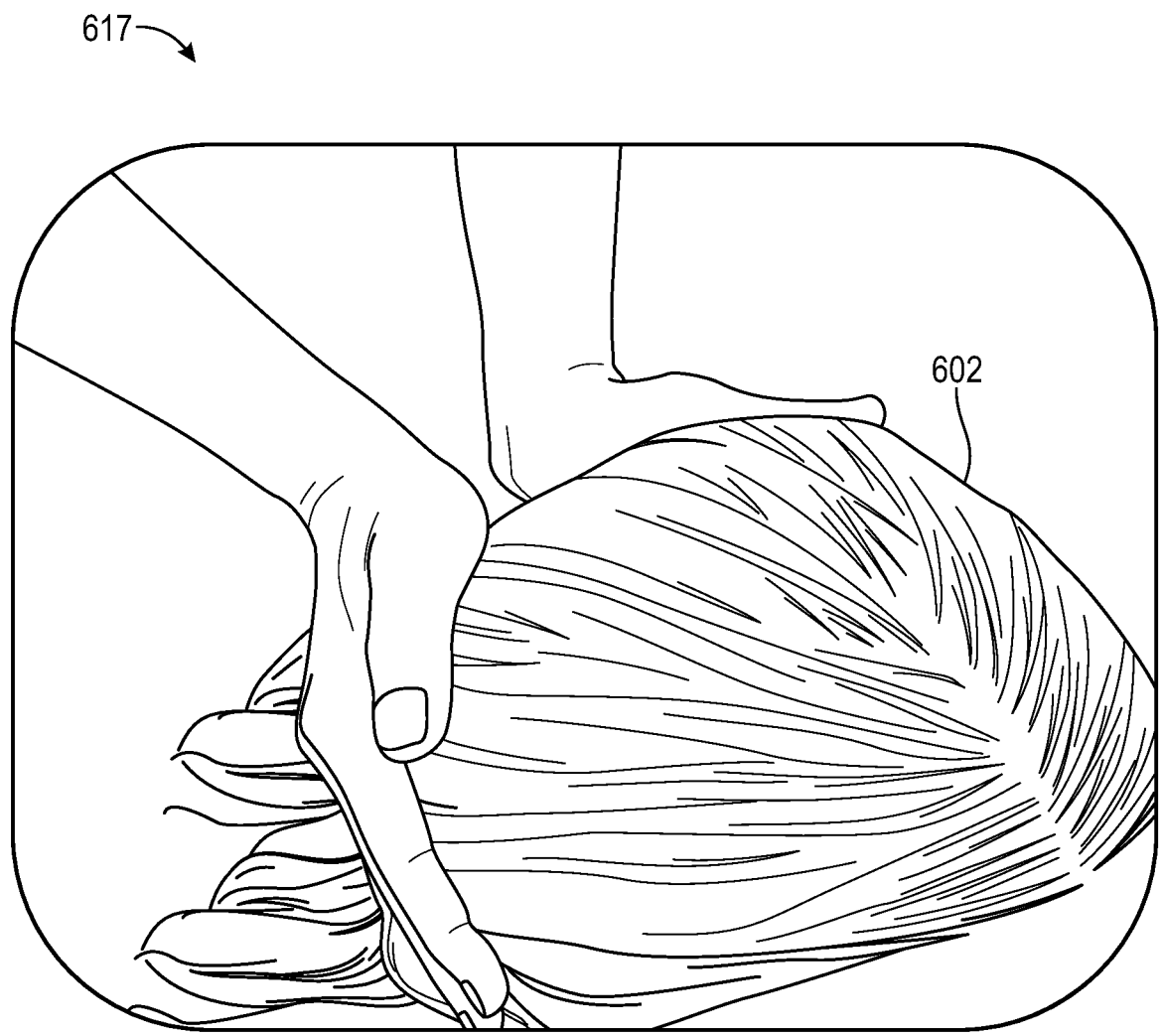
FIG. 6I shows a drawing of conditioning the now permed hair that may be applicable and/or representative of step 425 of method 400.

FIG. 4 may depict a flow diagram of a method 400. In some embodiments, method 400 may be a method of using kit/system 100 to perm hair. FIG. 4 may depict at least one step in method 400. FIG. 4 may depict one or more steps of method 400. In some embodiments, method 400 may be a method of using first-product 101 and using second-product 151 to perm hair. In some embodiments, the hair to be permed and/or that is permed by method 400 may be mammalian and/or human hair. In some embodiments, the hair to be permed and/or that is permed by method 400 may be head hair and/or scalp hair. In some embodiments, method 400 may comprise one or more steps of: step 401, step 403, step 405, step 407, step 409, step 411, step 413, step 415, step 417, step 419, step 421, step 423, step 425, step 427, step 429, portions thereof, combinations thereof, and/or the like. In some embodiments, at one of step 401, step 403, step 405, step 407, step 409, step 411, step 413, step 415, step 417, step 419, step 421, step 423, step 425, step 427, and/or of step 429 may be executed in numerical order with respect to reference numeral(s) of such steps. In some embodiments, at one of step 401, step 403, step 405, step 407, step 409, step 411, step 413, step 415, step 417, step 419, step 421, step 423, step 425, step 427, and/or of step 429 may be executed out of numerical order with respect to reference numeral(s) of such steps. In some embodiments, at one of step 401, step 403, step 405, step 407, step 409, step 411, step 413, step 415, step 417, step 419, step 421, step 423, step 425, step 427, and/or step 429 may be optional, skipped, and/or omitted. In some embodiments, at one of step of method 400 may be executed in numerical order with respect to reference numeral(s) of such steps. In some embodiments, at one of step of method 400 may be executed out of numerical order with respect to reference numeral(s) of such steps. In some embodiments, at one of step of method 400 may be optional, skipped, and/or omitted. Note in understanding method 400 and/or FIG. 4, FIG. 6A through and including FIG. 6I may also be reviewed, as FIG. 6A through and including FIG. 6I are intended to augment understanding of method 400 and/or of FIG. 4.

Continuing discussing FIG. 4, in some embodiments, step 401 may be a step of prepping the hair 602 to be treated/permed. See FIG. 6A showing a drawing 601 of prepping hair 602. Note, hair 602 is shown in FIG. 6A to FIG. 6I; however, its reference numeral of "602" is only used (called out) in FIG. 6A. Continuing discussing FIG. 4, in some embodiments, in executing step 401 the hair may be washed with a clarifying shampoo until the hair feels squeaky clean. In some embodiments, in executing step 401 the hair may be washed with a clarifying shampoo from one (1) to three (3) times in succession. In some embodiments, virgin and resistant coarse to medium hair need not be prepped with additional hair products. In some embodiments, virgin hair may be hair that has not been previously permed and/or bleached. In some embodiments, single processed, no bleach, and coarse to medium hair may be prepped with a product known in the hair styling industry as "Magic Spell." In some embodiments, virgin or single processed, no bleach, and fine hair may be prepped with "Magic Spell." In some embodiments, virgin or single processed, no bleach, and baby fine hair may be prepped with a hair conditioner, such as, "Revive Conditioner" (on the mids and ends of the hair). In some embodiments, previously bleached hair, porous highlights hair, and/or balayage hair, of any hair type, may be prepped with a hair conditioner, such as, "Revive Conditioner" (on the heavily lightened areas of the hair). In some embodiments, method 400 may progress from step 401 to step 403 and/or to step 405. See also FIG. 5 of Table 3 which may include at least some details/information as to how to prep hair in step 401.

Continuing discussing FIG. 4, in some embodiments, step 403 may be a step of attaching one or more support-structure(s) to the hair and/or placing the hair into supported shapes (e.g., twist knots and/or braids). In some embodiments, the support-structures may be on the rod types and/or off-the-rod types. See e.g., FIG. 6B of a drawing 603 of rolling rods 604 (e.g., a type of support-structures) onto hair 602. Continuing discussing FIG. 4, in some embodiments, the support-structures may be physical articles such as, but not limited to: perming tool; hair rods/curling rods (shown in FIG. 6B through and including FIG. 6G); hair clips (shown in FIG. 8A and/or in FIG. 8C); hair rods/pins/dowels (shown in FIG. 8B); portions thereof; combinations thereof; and/or the like. Additionally, in some embodiments, placing the hair into twist knots, braids, and/or the like (shown in FIG. 8B and/or in FIG. 8D) may be equivalent to attaching the hair to support-structure(s) and thus considered as encompassed by step 403. Thus, step 403 may be a step of shaping the hair into a predetermined shape, wave, style, and/or texture, using support-structures, rods, off-the-rod tools, and/or off-the-rod setting techniques. In some embodiments, when the support-structure(s) may be rod(s), the attaching mechanic may be a rolling mechanic; i.e., step 403 may be a step of rolling rod(s) onto the hair and/or rolling the hair onto rod(s). In some embodiments, method 400 may progress from step 403 to step 405 (e.g., if step 405 has not yet been executed); from step 403 to step 407 (e.g., if re-apply condition(s) may be applicable); and/or from step 403 to step 409 (e.g., if step 405 has already been executed).

Continuing discussing FIG. 4, in some embodiments, step 405 may be a step of applying first-product 101 to the (clean) hair. See e.g., FIG. 6C of a drawing 605 showing first-product 101 being applied directly to hair 602. Continuing discussing FIG. 4, in some embodiments, step 405 may be a step of wetting the (clean) hair with first-product 101. In some embodiments, an applicator bottle with first-product 101 therein may be used to execute step 405. In some embodiments, in executing step 405, cowlick and/or fringe fix hair may receive at least one (1) ounce (oz) of first-product 101. In some embodiments, in executing step 405, partially permed hair, Pixie hair, and/or Barbering hair may receive at least 1.5 ounces (oz) of first-product 101. In some embodiments, in executing step 405, short hair (e.g., chin length or to collarbone length) may receive at least three (3) ounces (oz) of first-product 101. In some embodiments, in executing step 405, mid length hair (e.g., hair to shoulder blades) may receive at least four (4) ounces (oz) of first-product 101. In some embodiments, in executing step 405, long hair (e.g., past the shoulder blades) may receive at least five (5) ounces (oz) of first-product 101. In some embodiments, completion of step 405 should result in the hair being saturated/wet with first-product 101. In some embodiments, method 400 may progress from step 405 to step 407 (e.g., if re-apply condition(s) may be applicable); from step 405 to step 409 (e.g., if step 403 has been completed and re-apply condition(s) are not applicable); and/or from step 405 to step 403 (e.g., if step 403 has not yet been executed/completed).

Continuing discussing FIG. 4, in some embodiments, step 407 may be a step of reapplying the first-product 101 to the hair. In some embodiments, step 407 may be a step of rewetting the hair with first-product 101. In some embodiments, prior to executing step 407 the hair may have already received at least some first-product 101 (after the most recent hair washing/shampooing and/or the most recent hair conditioning). In some embodiments, an applicator bottle with first-product 101 therein may be used to execute step 407. In some embodiments, completion of step 407 should result in the hair being saturated/wet with first-product 101. In some embodiments, a (predetermined) re-apply condition may be one or more of: if the hair looks dry after step 403 and step 405; if first-product 101 was applied before attaching the support-structure(s) to the hair and the hair now appears to be dry; if step 405 was completed prior to step 403 and the hair now appears to be dry; for coarse/medium virgin and resistant hair where such hair is not visually showing signs of hair movement after thirty (30) minutes of processing (step 409); for coarse/medium single process and/or no bleach hair where such hair is not visually showing signs of hair movement after twenty (20) minutes of processing (step 409); for fine virgin or single process and/or no bleach hair where such hair is not visually showing signs of hair movement after twenty (20) minutes of processing (step 409); and/or for any hair type that has been previously bleached, is porous, has highlights, and/or balayage where such hair is not visually showing signs of hair movement after twenty (20) minutes of processing (step 409). In some embodiments, step 403, step 405, and/or step 409 may feed into step 407, if at least one of the above noted re-apply condition(s) is triggered and/or is applicable. In some embodiments, method 400 may progress from step 407 to step 409. In some embodiments, step 407 may be omitted, skipped, and/or optional. See also, FIG. 5 for at least some (predetermined) re-apply condition(s).

Continuing discussing FIG. 4, in some embodiments, step 409 may be a step of processing the hair that is wetted/saturated with first-product 101. In some embodiments, step 409 may be at least a waiting step, wherein at least a predetermined minimum amount of time is permitted to elapse while the hair may be wetted, saturated, and/or physically exposed to first-product 101 (and to the attached support-structure(s)). In some embodiments, during step 409 the hair that has been previously wetted/saturated with first-product 101 may be permitted to soak in such conditions for at least a predetermined minimum amount of time, such as, but not limited to, at least ten (10) minutes, at least fifteen (15) minutes, at least twenty (20) minutes, at least twenty-five (25) minutes, at least thirty (30) minutes, or at least thirty-five (35) minutes. In some embodiments, step 409 processing times may run from ten (10) minutes to forty-five (45) minutes. In some embodiments, step 409 processing times may run from ten (10) minutes to forty-five (45) minutes or longer, but less than two (2) hours. In some embodiments, for virgin and resistant coarse/medium hair step 409 may run from thirty-five (35) minutes to forty-five (45) minutes. In some embodiments, for single process, no bleach, coarse/medium hair step 409 may run from twenty (20) minutes to thirty-five (35) minutes. In some embodiments, for virgin or single process, no bleach, fine hair step 409 may run from fifteen (15) minutes to thirty (30) minutes. In some embodiments, for virgin or single process, no bleach, baby fine hair step 409 may run from ten (10) minutes to twenty (20) minutes. In some embodiments, for previous bleach/porous, highlights, and/or balayage hair step 409 may run from ten (10) minutes to twenty (20) minutes (and with no step 411). In some embodiments step 411 may be sub-step of step 409. In some embodiments, step 409 may progress to step 411 and then back to step 409 once step 411 may be complete. In some embodiments, during step 409 and/or during step 411, at least a majority of preexisting disulfide bonds of the hair may be broken. In some embodiments, method 400 may progress from step 409 to step 407 if at least one of the above noted re-apply condition(s) is triggered and/or is applicable (see e.g., the above discussion of step 407). In some embodiments, when at least ten (10) minutes of step 409 may be executed and/or implemented, then method 400 may progress to step 413. In some embodiments, when step 409 may be completed, then method 400 may progress to step 413. See also, FIG. 5 for average processing times of step 409 for different hair types.

Note, times (durations) noted herein may be plus or minus five (5) minutes in some embodiments.

Continuing discussing FIG. 4, in some embodiments, step 411 may be a step of capping and heating the hair 602 that is wetted/saturated with first-product 101. See e.g., FIG. 6D of a drawing 607 of allowing hair 602 to process with first-product 101, while capped with a plastic bag 608a (processing cap 608a) and heated with at least one heater 608b. Continuing discussing FIG. 4, in some embodiments, the capping of step 411 may entail placing a (transparent) plastic bag 608a (processing cap 608a) over the hair 602 with the support-structure(s) (already attached to the hair 602) and wherein that hair 602 is wetted/saturated with first-product 101 (see e.g., FIG. 6D). In some embodiments, the heating of step 411 may entail creating a warm environment to the capped hair with an infrared light(s) 608b, a climazone, and/or a handheld diffuser, with such heating means on medium heat and/or on medium speed. In some embodiments, a hood dryer may also be used for the step 411 heating; however, use of the infrared light(s) 608b, the climazone, and/or the handheld diffuser may be preferred over use of the hood dryer. In some embodiments, use of a heated hood dryer is not recommended for such heating of step 411.

Continuing discussing FIG. 4, in some embodiments, with respect to the "if predetermined conditions are met" language shown in step 411 of FIG. 4, step 411 should be executed as soon as step 409 is implemented, such as, but not limited to: for virgin and resistant coarse/medium hair; and/or for single process, no bleach, coarse/medium hair. In some embodiments, with respect to the "if predetermined conditions are met" language shown in step 411 of FIG. 4, step 411 should be executed after ten (10) minutes of processing of step 409 and there has not been no (significant) visual movement of the hair, such as, but not limited to: for single process, no bleach, fine hair; and/or for virgin or single process, no bleach, baby fine hair. In some embodiments, with respect to the "if predetermined conditions are met" language shown in step 411 of FIG. 4, step 411 may be skipped and/or omitted for hair that has had a previous bleach, porous, highlights, or balayage. In some embodiments, method 400 may progress from step 411 to step 409.

Continuing discussing FIG. 4, in some embodiments, step 413 may be a step of performing and/or executing an elasticity test of the hair 602 that has been processing according to step 409 and/or to step 411. In some embodiments, during the elasticity test of step 413, at least some hair 705 may be separated from at least one support-structure, such that from one (1) to a dozen (12) hair strands may be physically handled/manipulated during the elasticity test. In some embodiments, it may be from one (1) to three (3) such strands 705 that may be separated for physical handling/manipulation. In some embodiments, those separated hair strands 705 are held in each hand of a person such that there is a distance of about one (1) inch to about four (4) inches between the two hands, with the separated hair strands 705 spanning that distance. See e.g., FIG. 6E of drawing 609 showing this aspect of the elasticity test. Continuing discussing FIG. 4, in some embodiments, then those hair strands 705 are gently pulled on by the two hands in opposite directions from each other such that those hair strands 705 are placed under tension (see e.g., FIG. 7, left-side drawing 701) and that tension is released (see e.g., FIG. 7, right-side drawing 703). Continuing discussing FIG. 4, in some embodiments, if those separated hair strands 705 exhibit elastic behavior by springing/bouncing back towards itself after the release of the tension, like a fresh rubber band would behave, then this step 413 elasticity test may be passed and method 400 may progress from step 413 to step 415 (and/or to step 417). Whereas, if those separated hair strands 705 do not exhibit this elastic (spring/bounce) behavior after the tension is released, then this step 413 elasticity test may be failed and method 400 may progress from step 413 to step 429. See also, FIG. 6E and FIG. 7 for drawings illustrating an elasticity test of step 413.

Continuing discussing FIG. 4, in some embodiments, step 415 may be a step of applying second-product 151 (directly) to the hair that has been wetted/saturated with first-product 101; without first rinsing the hair of the first-product 101. In some embodiments, this step 415 may also then be framed and/or characterized as a step of neutralizing over the top, as in the second-product 151 is applied directly to the hair 602 that has the first-product 101 mixed into the hair 602 and without first rinsing the first-product 101 out of the hair 602 before applying the second-product 151. See e.g., FIG. 6F showing a drawing 611 of second-product 151 being applied directly over the top to hair 602 that has first-product 101 already mixed in with hair 602 and without first rinsing first-product 101 out of the hair 602 before applying second-product 151. It is this this ability to apply the second-product 151 directly to the hair, with the first-product 101, without first rinsing out the first-product 101 is what allows new and novel hair perms to be done on hair (e.g., using off-the-rod techniques/tools); particularly hair with delicately formed shapes. In some embodiments, hair with a delicately formed shaped, may be hair formed into at least one shape with off-the-rod tools and/or off-the-rod techniques. Note, FIG. 8A to FIG. 8D show examples of such hair with a delicately formed shapes. Continuing discussing FIG. 4, in some embodiments, the volume and/or the amount of second-product 151 applied to the hair 602 may be from 1.5 times to two (2) times the volume/amount of first-product 101 used on the hair 602. In some embodiments, method 400 may progress from step 415 to step 417.

Continuing discussing FIG. 4, in some embodiments, step 417 may be a step of placing/adjusting the hair into the final desired shape, style, and/or texture; and/or step 417 may be a step of making sure the hair is in the final desired shape, style, and/or texture; and if not, then making the necessary adjustments to the support-structure(s), braids, and/or twist knots to arrive at the final desired shape, style, and/or texture of the hair. In some embodiments, step 415 and step 417 may be executed concurrently with each other or at least partially so; step 417 may be begun before step 415; step 415 may be begun before step 417; portions thereof; combinations thereof; and/or the like; however, both step 415 and step 417 may be complete before method 400 progresses to step 419. Accordingly, in some embodiments, a successful pass of the step 413 elasticity test may progress method 400 to step 415 and/or to step 417.

Continuing discussing FIG. 4, in some embodiments, step 419 may be a step of allowing sufficient time for the applied second-product 151 to neutralize the effects of the first-product 101, which in turn allows the hair to regenerate/reform appropriate disulfide bonds to maintain of the final desired shape, style, and/or texture the hair. Thus, step 419 may be a neutralizing and/or regeneration step. And/or step 419 may be a step of locking in the final desired shape, style, and/or texture the hair. In some embodiments, the low acidic pH of second-product 151 and/or the oxidating agent of second-product 151 contribute to neutralizing the effects of first-product 101 on the hair. In some embodiments, step 419 may go on for a minimum of ten (10) minutes. In some embodiments, step 419 may go on for a maximum of twenty (20) minutes. In some embodiments, step 419 may go on for ten (10) minutes for finer hair and/or for more compromised textures and up to twenty (20) minutes for very resistant hair. In some embodiments, step 419 may go on for fifteen (15) minutes for most hair types and textures. In some embodiments, for virgin and resistant coarse/medium hair; for single process, no bleach, coarse/medium hair; and/or for virgin or single process, no bleach, fine hair, step 419 may go on for fifteen (15) minutes. In some embodiments, for virgin or single process, no bleach, baby fine hair; and/or for previous bleach/porous highlights or balayage hair, step 419 may go on for ten (10) minutes. In some embodiments, step 415, step 417, and/or step 419 may not include heating the hair nor capping the hair. In some embodiments, method 400 may progress from step 419 to step 421. See also, FIG. 5 for details on neutralizing times.

Continuing discussing FIG. 4, in some embodiments, step 421 may be a step of removing the support-structures (such as, but not limited to, rods, perm tools, and/or the like), if any, from the hair. See e.g., FIG. 6G of a drawing 613 showing rods 604 being removed from hair 602. In some embodiments, if an off-the-rod set/tool was used, then step 421 may entail undoing/releasing the off-the-rod set (e.g., undoing/release twist knots and/or braids). In some embodiments, method 400 may progress from step 421 to step 423.

Continuing discussing FIG. 4, in some embodiments, step 423 may be a step of rinsing the hair with water to remove both first-product 101 and second-product 151 from the hair 602. See e.g., FIG. 6H of a drawing 615 of hair 602 being rinsed of both first-product 101 and/or second-product 151. In some embodiments, executing of step 423 may use lukewarm water. In some embodiments, step 423 may be complete when the hair feels squeaky clean to the touch. In some embodiments, method 400 may progress from step 423 to step 425.

Continuing discussing FIG. 4, in some embodiments, step 425 may be a step of conditioning the hair 602 with a conditioner. See e.g., FIG. 6I of a drawing 617 of applying a conditioner to hair 602. In some embodiments, the conditioner may be a conditioner called "Revive Hydrating Conditioner." In some embodiments, this conditioner may be a hydrating conditioner that may be rinsed out of the hair 602. In some embodiments, this conditioner is not a leave-in conditioner. In some embodiments, method 400 may progress from step 425 to step 427. In some embodiments, method 400 may end/terminate at step 425.

Continuing discussing FIG. 4, in some embodiments, step 427 may be a step of styling the hair. In some embodiments, while the hair may be (very) wet, almost dripping, apply a product called "Magic Spell Conditioning Leave-In" to the hair. In some embodiments, then detangle the hair with a wide tooth comb. In some embodiments, then use one (1) to two (2) pumps of "Enhance Moisturizing Curl Cream" onto the hair. In some embodiments, then dry the hair with a microfiber towel (or the like) and/or squeeze water out of the hair. In some embodiments, air drying or gently diffusing may be appropriate for drying. In some embodiments, method 400 may end/terminate at completion of step 427.

Continuing discussing FIG. 4, in some embodiments, step 429 may be a step of preparing to re-do the step 413 elasticity test. In some embodiments, during step 429 re-attach the hair to the support-structure(s) and allow processing (waiting) to occur for at least ten (10) minutes before re-executing the step 413 elasticity test. In some embodiments, method 400 may progress from step 429 back to step 413, i.e., to repeat the step 413 elasticity test.

In some embodiments method 400 may be a method of perming mammalian hair. In some embodiments, in at least some of the claims, claimed step (a) may be the same and/or equivalent to step 405; claimed step (b) may be the same and/or equivalent to step 403; claimed step (c) may be the same and/or equivalent to step 409; claimed step (d) may the same and/or equivalent to step 413; and claimed step (e) may be the same and/or equivalent to step 415. In some embodiments, method 400 may comprise step (a), step (b), step (c), step (d), and step (e). In some embodiments, step (a) may be a step of applying the first-composition (first-product 101) comprising water and cysteamine HCl to at least some of the mammalian hair (see e.g., step 405). In some embodiments, step (b) may be a step of shaping the at least some mammalian hair by attaching at least one support-structure to the at least some mammalian hair and/or by using at least one off-the-rod setting technique to shape the at least some mammalian hair (see e.g., step 403). In some embodiments, step (c) may be a step of waiting at least ten (10) minutes while the at least some mammalian hair has been shaped from the step (b) and while the at least some mammalian hair had the first-composition applied to the at least some mammalian hair from the step (a); wherein execution of the step (c) is configured to break at least some preexisting disulfide bonds in the at least some mammalian hair (see e.g. step 409). In some embodiments, step (d) may be a step of testing elasticity of at least one strand of hair selected from the at least some mammalian hair (see e.g., step 413). In some embodiments, step (e) may be a step of (directly) applying the second-composition (e.g., second-product 151) to the at least some mammalian hair that has the first-composition without first rinsing the at least some mammalian hair (see e.g., step 415), if the at least some mammalian hair passed the step (d) elasticity test. In some embodiments, the second-composition may be configured to stop the first-composition from breaking any further disulfide bonds in the at least some mammalian hair, which in turn may prevent the at least some mammalian hair from forming any undesired shapes. In some embodiments, if the step (d) (step 413) elasticity test failed (was not passed), then method 400 instead of executing step (e), may repeat the step (b) and the step (c), which may be the same and/or equivalent to method 400 executing step 429. See e.g., FIG. 4.

In some embodiments, the at least some mammalian hair passes the step (d) elasticity test (step 413) when the at least one strand of hair recoils to half of a distance or more of the at least one strand of hair after tension is released from the at least one strand of hair. In some embodiments, the at least some mammalian hair fails the step (d) elasticity test when the at least one strand of hair fails to recoil half of the distance or more of the at least one strand of hair after the tension is released from the at least one strand of hair. As explained above in step 413 and/or as shown in FIG. 7, this tension is applied by human hands holding the at least one strand of hair. Essentially, the at least one strand of hair is stretched in manner that a rubber band could be stretched by a pair of hands and the elasticity (or lack thereof) of that tested at least one strand of hair is tested in the step (d) (step 413).

In some embodiments, during the step (c) the at least some mammalian hair is at least mostly capped with at least one plastic sheet and/or at least partially heated, wherein here the step (c) may refer to step 409 and to step 411. In some embodiments, such heating may be done by one or more of: an infrared light; a climazone; and/or a handheld diffuser on a medium heat setting and/or on a medium speed setting. In some embodiments, such heating may be done by one or more of: the infrared light, the climazone, the handheld diffuser on the medium heat setting and/or on the medium speed setting; and/or a hood dryer.

In some embodiments, after the step (e), method 400 may further comprise a step of waiting at least ten (10) minutes to permit the second-composition to stop the first-composition from breaking the any further disulfide bonds in the at least some mammalian hair (see e.g., step 419). In some embodiments, such neutralization of the first-composition by the directly applied second-composition and by such waiting, the at least some mammalian hair may be prevented from forming into any undesired shapes and may rather maintain the desired shape by virtue of the at least one hair attached support-structure (e.g., rod(s)), the off-the-rod technique, and/or the hair attached off-the-rod tool(s). In some embodiments, after step 419 method 400 may further comprise a step of removing the at least one support-structure from the at least some mammalian hair and/or of undoing the at least one off-the-rod setting technique from the at least some mammalian hair (see e.g., step 421). In some embodiments, after step 421 method 400 may further comprise a step of rinsing the at least some mammalian hair with water to remove the first-composition and to remove the second-composition from that at least some mammalian hair (see e.g., step 423). In some embodiments, after step 423 method 400 may further comprise a step of conditioning the at least some mammalian hair with at least one hair conditioner (e.g., step 425). In some embodiments, after step 425 method 400 may further comprise a step of styling the at least some mammalian hair (e.g., step 427).

In some embodiments, before the step (a) and before the step (b), method 400 further comprises a step of prepping the at least some mammalian hair by washing the at least some mammalian hair with at least one hair shampoo (e.g., step 401).

In some embodiments, the step (b) may be started before starting the step (a), wherein the step (a) and the step (b) may both be completed before the step (c) may be implemented. See e.g., FIG. 4.

In some embodiments, the step (a) may be repeated before the step (e) is executed if at least one predetermined re-apply condition is triggered (see e.g., step 407).

In some embodiments, with respect to step (b) (step 403) and/or to step 421, the at least one support-structure may be selected from one or more of: a hair rod, a hair curling rod, a perm tool, a hair clip, a cotton swab, a dowel, or a pin. In some embodiments, with respect to step (b) (step 403) and/or to step 421, the at least one off-the-rod setting technique may be at least one of: a wave, a braid, a finger wave, and/or a twist knot implemented in the at least some mammalian hair. In some embodiments, with respect to step (b) (step 403) and/or to step 421, an off-the-rod tool may comprise a two-pronged hair clip.

FIG. 5 may depict Table 3 which may depict at least some information/details pertaining to various steps of method 400. In some embodiments, Table 3 (FIG. 5) may be referred to as a processing guide. In some embodiments, for hair of different color histories and hair types, Table 3 (FIG. 5) may show: how the hair may be prepped (e.g., step 401); whether and how the hair may be capped and heated (e.g., step 411); at least some the (predetermined) re-apply conditions (e.g., step 407); average processing times (e.g., step 409); and average neutralizing times (e.g., step 419). In some embodiments, the hair of different color histories and hair types addressed in Table 3 (FIG. 5) may be: virgin and resistant coarse/medium hair; single process, no bleach, coarse/medium hair; virgin or single process, no bleach, fine hair; virgin or single process, no bleach, baby fine hair; and previous bleach/porous—highlights or balayage hair (or any hair type). In some embodiments, FIG. 5 (Table 3) may be used in conjunction with FIG. 4 and/or with at least some steps of method 400. In some embodiments, Table 3 (FIG. 5) may be intended as a guide and not immutable laws/rules.

FIG. 6A through and including FIG. 6I may show at least some aspect of method 400, but instead of using a flowchart like in FIG. 4, by using drawings representative of at least some of the steps of method 400. In some embodiments, drawing 601 shown in FIG. 6A may be applicable to prepping step 401. In some embodiments, drawing 603 shown in FIG. 6B may be applicable to step 403. In some embodiments, drawing 605 shown in FIG. 6C may be applicable to step 405. In some embodiments, drawing 607 shown in FIG. 6D may be applicable to step 409 and/or to step 411. In some embodiments, drawing 609 shown in FIG.

6E may be applicable to (elasticity test) step 413. In some embodiments, drawing 611 shown in FIG. 6F may be applicable to step 415, step 417, and step 419, i.e., to the neutralizing and the regenerating steps to lock in the final desired shape, style, and/or texture of the hair. In some embodiments, drawing 613 shown in FIG. 6G may be applicable to (removing/undoing support-structure(s) from hair) step 421. In some embodiments, drawing 615 shown in FIG. 6H may be applicable to (hair rinsing) step 423. In some embodiments, drawing 617 shown in FIG. 6I may be applicable to (hair conditioning) step 425. FIG. 6A through and including FIG. 6I may compliment the discussion and/or understanding of FIG. 4 and/or of method 400.

Figure 7:
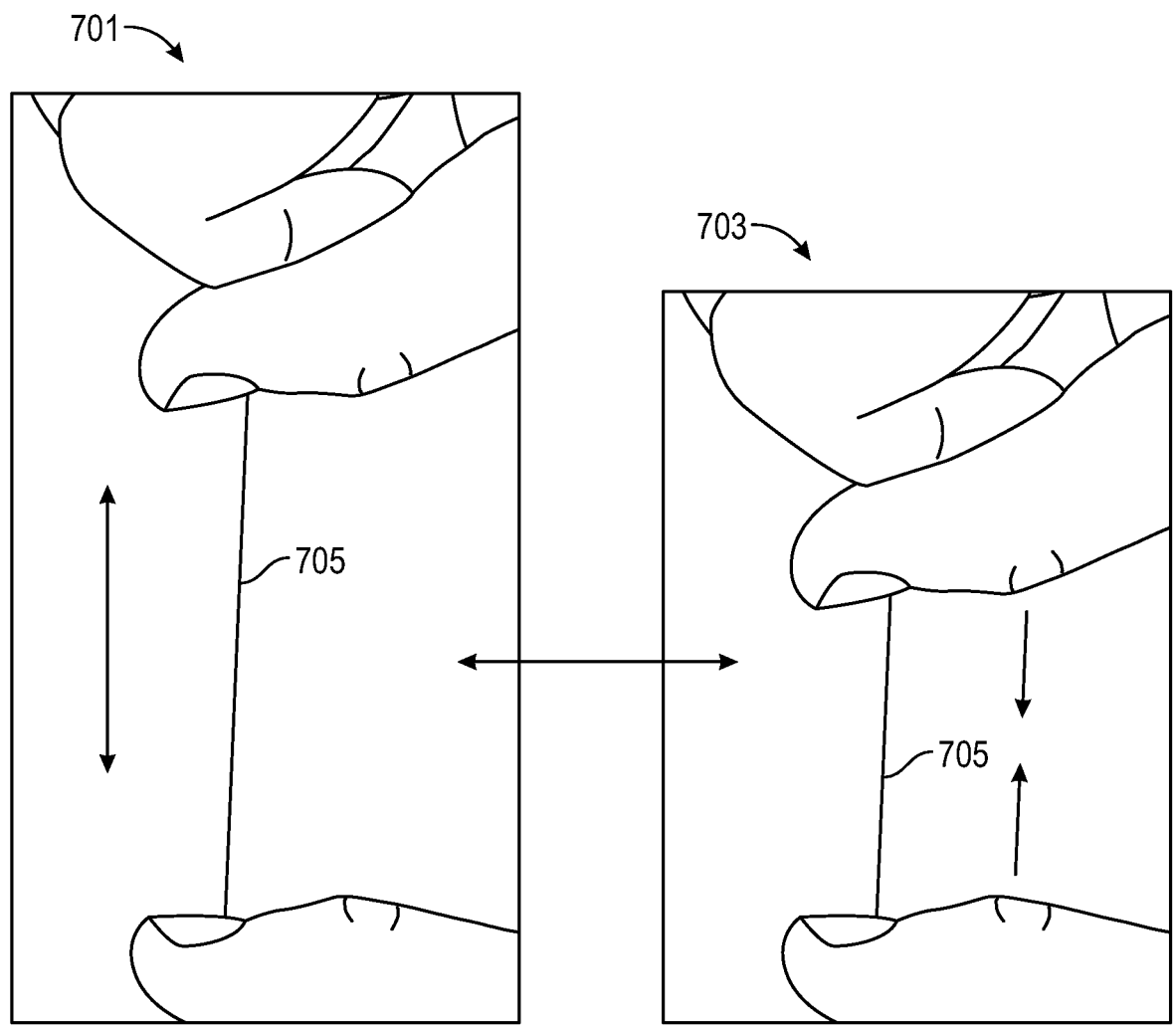
FIG. 7 using two (2) side-by-side drawings may show how a hair elasticity test may be implemented/executed.

FIG. 7 using drawings may show how the step 413 elasticity test may be implemented/executed. FIG. 7 shows two drawings 701 and 703 with hair strand(s) 705 that have been separated out from the rest of the scalp hair in order to perform the step 413 elasticity test on. These separated hair strands may be gripped in both ends, such that a distance of about four (4) inches to about one (1) inch is between the two hands, with the separated hair strands spanning that distance. Each hand may use a finger and thumb to grip one end of the separated strand(s) 705 of hair as shown in FIG. 7. The left side drawing 701 in FIG. 7 shows the separated hair strand(s) 705 under tension, by the hand gently pulling in opposite directions on those separated hair strand(s). Whereas, the right-side drawing 703 in FIG. 7 shows the separated hair strand(s) in a state where that tension has been released, wherein if the hair is now sufficiently elastic, the separated hair strand(s) in this relaxed (but still gripped) state will have a reduced distance due to the elastic force. In some embodiments, when a given tester executes the step 413 elasticity test, that tester may alternate between left-side drawing 701 and right-side drawing 703; and/or that tester may begin with either of the two different and opposing configurations shown in left-side drawing 701 or right-side drawing 703. For example, under a passing elasticity test: if the hair strand(s) 705 were about four (4) inches when under tension as in left-side drawing 701 and then those strand(s) 705 may contract to about two (2) inches when relaxed as in right-side drawing 703; if the hair strand(s) 705 were about three (3) inches when under tension as in left-side drawing 701 and then those strand(s) 705 may contract to about 1.5 inches when relaxed as in right-side drawing 703; if the hair strand(s) 705 were about two (2) inches when under tension as in left-side drawing 701 and then those strand(s) 705 may contract to about one (1) inches when relaxed as in right-side drawing 703; and/or the like.

Figure 8A:
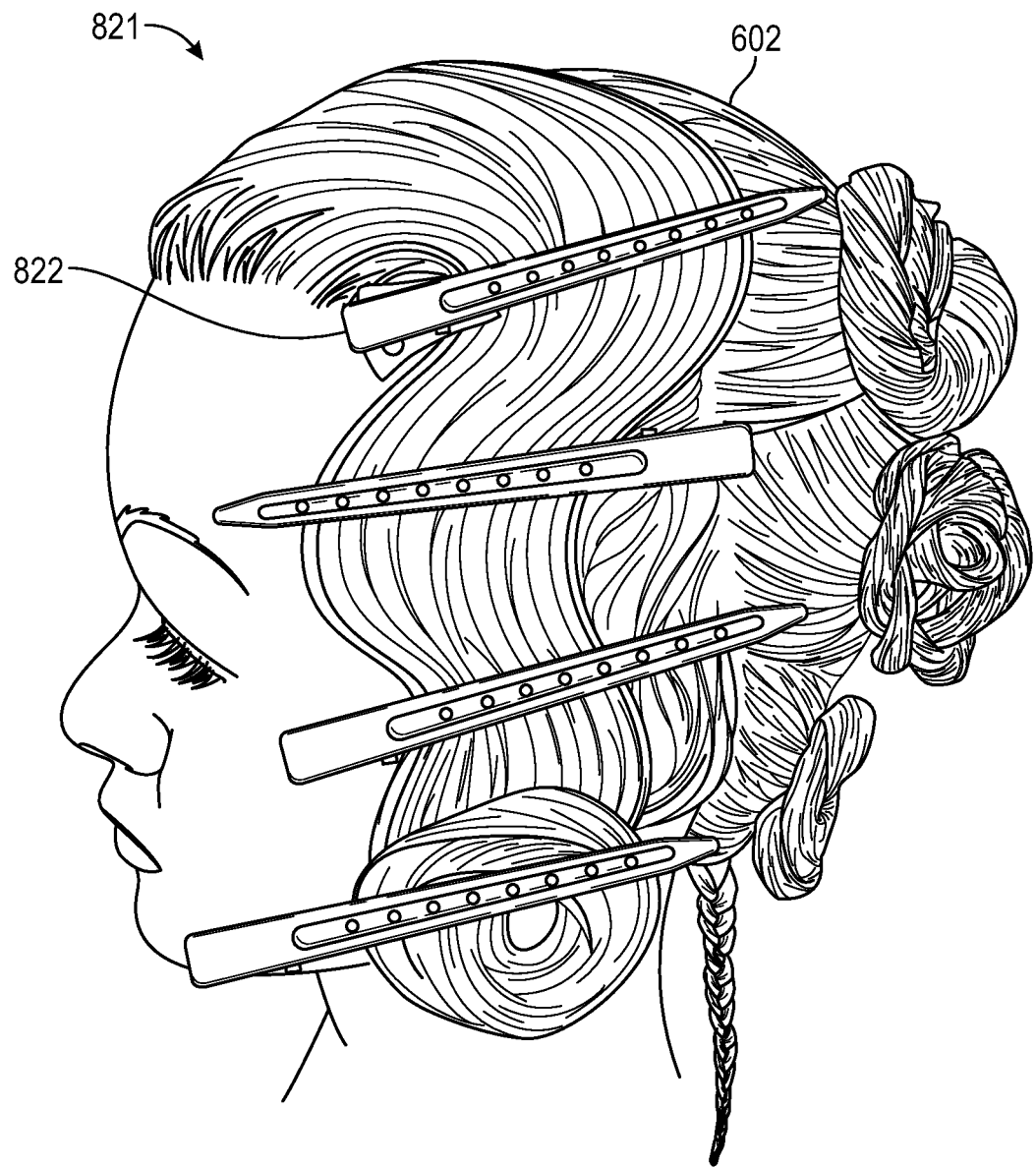
FIG. 8A may show an off-the-rod setting technique that may be an alternative to (or in addition to) rods and/or to perm tools.

FIG. 8A may show an off-the-rod setting technique 821 that may be an alternative to (or in addition to) rods and/or to perm tools. Specifically, hair clips 822 may be used to form and maintain various predetermined hair waves. Such hair clips 822 and the wave structure may be seen on the side of the head in FIG. 8A. Additionally, the back of the head in FIG. 8A shows twist knots being used as another off-the-rod setting technique. Further still, the back rear of the head shows a braid descending from the head as yet another off-the-rod setting technique.

Figure 8B:
FIG. 8B shows a top rear perspective view of a head of a person with twist knots being employed as an off-the-rod setting technique.

FIG. 8B shows a top rear perspective view of a head of a person with twist knots 823 being employed as an off-the-rod setting technique. In some embodiments, elongate members, such as, but not limited to, cotton swabs, q-tips, dowels, and/or pins, may be used with the twist knots 823, used to help form, hold, and/or maintain the twist knots 823.

Figure 8C:
FIG. 8C shows a top perspective view of a head of a person with hair clips being employed as an off-the-rod setting technique to create a predetermined wave style in the hair.

FIG. 8C shows a top perspective view of a head of a person with hair clips 822 being employed as an off-the-rod setting technique 825 to create a predetermined wave style in the hair. Note, the hair clips 822 used and/or shown in FIG. 8A and/or in FIG. 8C may be made mostly (substantially) from one or more metals and/or metal alloys and/or may be plated/covered at least substantially (mostly) in one or more metals and/or metal alloys, such as, but not limited to, tin, steel, stainless steel, iron, aluminum, chrome, portions thereof, combinations thereof, and/or the like. In some embodiments, first-product 101 and/or second-product 151 are compatible with using metal/metallic perming tools, rods, off-the-rod tools/techniques, portions thereof, and/or the like. In some embodiments, first-product 101 and/or second-product 151 may be non-reactive and/or non-corrosive with using metal/metallic perming tools, rods, off-the-rod tools/techniques, portions thereof, and/or the like.

Figure 8D:
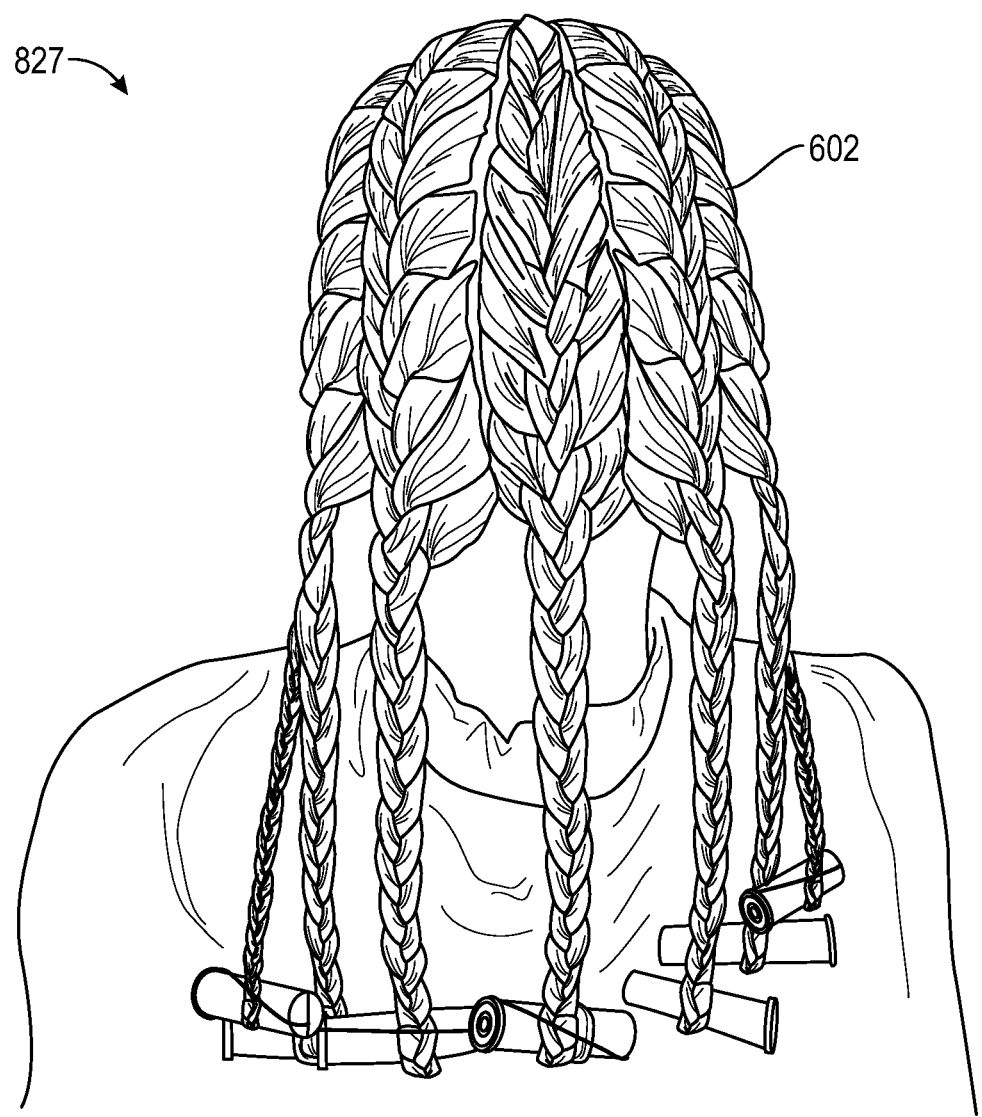
FIG. 8D shows a rear perspective view of a head of a person with braids being employed as an off-the-rod setting technique to create a predetermined style in the hair.

FIG. 8D shows a rear perspective view of a head of a person with braids 827 being employed as an off-the-rod setting technique to create a predetermined style in the hair. In some embodiments, other styles and/or types of hair braids may be employed/utilized other than the type of braids shown in FIG. 8D.

In some embodiments, off-the-rod setting techniques and/or tools of FIG. 8A, FIG. 8B, FIG. 8C, FIG. 8D, portions thereof, combinations thereof, and/or the like may be used in step 403. In some embodiments, off-the-rod setting techniques and/or tools such as, but not limited to, braids, hair clips, cotton swabs, dowels, rods (not perming rods), hair twists, hair waves, portions thereof, combinations thereof, and/or the like may be used in step 403.

In some embodiments, first-product 101 and second-product 151 are the only two solutions required to perm any and/or most types of (mammalian and/or human) hair. In some embodiments, first-product 101 and second-product 151 are the only two solutions required to perm all and/or most types of (mammalian and/or human) hair. Types of (mammalian and/or human) hair may comprise hair of different lengths, hair of different texture, hair of different texture, hair of different coarseness, hair of different thickness, hair of different natural wave and/or natural straightness, hair of different natural colors, hair of different applied colors, hair of different artificial colors, hair of different stages of bleaching/oxidation, hair of different applied lightening and/or shading, portions thereof, combinations thereof, and/or the like.

In some embodiments, unless otherwise noted, minute time periods denoted herein may be plus or minus five (5) minutes.

First-product 101 and second-product 151 may be free of (without): ammonia, thioglycolic acid, sulfate surfactants, and/or parabens.

Method 400 may be a cold and/or a clean wave perm, in that no to minimal heat is used in the perming process.

Method 400 may neutralize without rinsing, simply by applying second-product 151 to the hair with the first-product 101; whereas, prior art hair perming means require the thioglycolic acid (perm solution) to be rinsed out first and then after that intervening rinse out step any residual thioglycolic acid is neutralized with application of some form of neutralizer to the hair. In prior art hair perming means there are at least two separate rinsing out phases, the intervening rinse out and a final rinse out. Whereas, in method 400 there is only one and final rinse out step, after the second-product 151 has neutralized the first-product 101; and never the intervening rinse step.

Note, method 400 may save fifteen (15) gallons of water or more per perm session as compared against prior art hair perming methods.

In some embodiments, perming hair as taught herein (e.g., via method 400 and using first-product 101 and using second-product 151) may result in hair that does not smell bad as compared against prior art hair perming processes. In some embodiments, applying the second-product 151 directly over (on top of) the hair with the first-product 101 still mixed in with hair (e.g., step 415), may substantially reduce to eliminate undesirable smells and/or odors associated with (and/or emanating) from first-product 101. In some embodiments, once the second-product 151 is directly applied over (on top of) the hair with the first-product 101 still mixed in with hair (e.g., step 415), then the hair may have no offensive smells and/or odors.

In some embodiments, perming hair as taught herein (e.g., via method 400 and using first-product 101 and using second-product 151) may result in hair that is softer, shinier, healthier, and/or the like as compared against that hair before such perming treatment. For example, and without limiting the scope of the present invention, forty-three (43) out of fifty-six (56) people or 77% surveyed said that their hair was softer and shinier after receiving the hair perm as taught herein; and 14% reported no change in hair softness/health before and after the hair perm as taught herein. That is, over 90% of customers/clients surveyed had no change or had softer and healthier hair after the hair perm as compared to before the hair perm (wherein the hair perm was conducted pursuant to method 400). See e.g., FIG. 9 shows a Table 4 that is of this survey data with respect to hair softness, hair health (e.g., degree of shine and/or dryness), and/or hair damage before and after perming pursuant to method 400.

Compositions, products, systems, kits, and/or method of perming (human and/or mammalian) (head and/or scalp) hair have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method of perming mammalian hair comprising steps of:
    a step (a) of applying a first-composition comprising water, cysteamine HCl, and cysteine HCl to at least some of the mammalian hair;
    a step (b) of shaping the at least some mammalian hair by attaching at least one support-structure to the at least some mammalian hair and/or by using at least one off-the-rod setting technique to shape the at least some mammalian hair;
    a step (c) of waiting at least ten (10) minutes while the at least some mammalian hair has been shaped from the step (b) and while the at least some mammalian hair had the first-composition applied to the at least some mammalian hair from the step (a); wherein execution of the step (c) is configured to break at least some preexisting disulfide bonds in the at least some mammalian hair;
    a step (d) testing an elasticity of at least one strand of hair selected from the at least some mammalian hair; and
    a step (e) of applying a second-composition to the at least some mammalian hair, if the at least some mammalian hair passes the step (d) elasticity test; wherein the second-composition is configured to stop the first-composition from breaking any further disulfide bonds in the at least some mammalian hair; wherein the at least some of the mammalian hair is not rinsed between application of the first-composition and application of the second-composition; or
    repeating the step (b) and the step (c) if the at least some mammalian hair fails the step (d) elasticity test.

2. The method according to claim 1, wherein the at least some mammalian hair passes the step (d) elasticity test when the at least one strand of hair recoils to half of a distance or more of the at least one strand of hair after tension is released from the at least one strand of hair; and wherein the at least some mammalian hair fails the step (d) elasticity test when the at least one strand of hair fails to recoil half of the distance or more of the at least one strand of hair after the tension is released from the at least one strand of hair.

3. The method according to claim 1, wherein during the step (c) the at least some mammalian hair is at least mostly capped with at least one plastic sheet.

4. The method according to claim 1, wherein during the step (c) the at least some mammalian hair is at least partially heated.

5. The method according to claim 4, wherein the heating is done by one or more of: an infrared light, a climazone, or a handheld diffuser on a medium heat setting and/or on a medium speed setting.

6. The method according to claim 1, wherein after the step (e), the method further comprises a step of waiting at least ten (10) minutes to permit the second-composition to stop the first-composition from breaking the any further disulfide bonds in the at least some mammalian hair.

7. The method according to claim 6, wherein the method further comprises a step of removing the at least one support-structure from the at least some mammalian hair and/or of undoing the at least one off-the-rod setting technique from the at least some mammalian hair.

8. The method according to claim 7, wherein the method further comprises a step of rinsing the at least some mammalian hair with water to remove the first-composition and to remove the second-composition.

9. The method according to claim 8, wherein the method further comprises a step of conditioning the at least some mammalian hair with at least one hair conditioner.

10. The method according to claim 9, wherein the method further comprises a step of styling the at least some mammalian hair.

11. The method according to claim 1, wherein before the step (a) and before the step (b), the method further comprises a step of prepping the at least some mammalian hair by washing the at least some mammalian hair with at least one hair shampoo.

12. The method according to claim 1, wherein the step (b) is started before starting the step (a), wherein the step (a) and the step (b) are both completed before the step (c) is implemented.

13. The method according to claim 1, wherein the step (a) is repeated before the step (e) if at least one predetermined re-apply condition is triggered.

14. The method according to claim 1, wherein the at least one support-structure is selected from one or more of: a hair rod, a hair curling rod, a perm tool, a hair clip, a cotton swab, a dowel, or a pin.

15. The method according to claim 1, wherein the at least one off-the-rod setting technique is at least one of a wave, a braid, and/or a twist knot implemented in the at least some mammalian hair.

16. The method according to claim 1, wherein execution of the step (e) eliminates odors associated with the first-composition.

\* \* \* \* \*